(12) United States Patent
Chase et al.

(10) Patent No.: US 9,820,739 B2
(45) Date of Patent: *Nov. 21, 2017

(54) SKIN STAPLER WITH COMPONENTS OPTIMIZED FOR CONSTRUCTION WITH PLANT BASED MATERIALS

(71) Applicants: Robert N Chase, San Rafael, CA (US); Paul Kardel, Corte Madera, CA (US)

(72) Inventors: Robert N Chase, San Rafael, CA (US); Paul Kardel, Corte Madera, CA (US)

(73) Assignee: NEWGEN SURGICAL, INC., San Rafael, CA (US)

( * ) Notice: Subject to any disclaimer, the term of this patent is extended or adjusted under 35 U.S.C. 154(b) by 478 days.

This patent is subject to a terminal disclaimer.

(21) Appl. No.: 14/609,938

(22) Filed: Jan. 30, 2015

(65) Prior Publication Data

US 2015/0136834 A1    May 21, 2015

Related U.S. Application Data

(63) Continuation-in-part of application No. 14/155,106, filed on Jan. 14, 2014, now Pat. No. 9,572,575, which
(Continued)

(51) Int. Cl.
| | |
|---|---|
| *A61B 17/04* | (2006.01) |
| *A61B 17/10* | (2006.01) |
| *A61B 17/068* | (2006.01) |
| *A61B 17/064* | (2006.01) |
| *A61B 17/00* | (2006.01) |

(Continued)

(52) U.S. Cl.
CPC ...... *A61B 17/0684* (2013.01); *A61B 17/0644* (2013.01); *A61B 50/36* (2016.02); *A61B 2017/0023* (2013.01); *A61B 2017/0688* (2013.01); *A61B 2017/2946* (2013.01); *A61B 2090/037* (2016.02)

(58) Field of Classification Search
CPC ........... A61B 2017/07271; A61B 2017/07278; A61B 2017/0053
USPC ........................................ 227/175.1–182.1
See application file for complete search history.

(56) References Cited

U.S. PATENT DOCUMENTS

| | | | |
|---|---|---|---|
| 4,411,378 A | 10/1983 | Warman | |
| 5,407,118 A * | 4/1995 | Marks | ..... B25C 5/085 227/132 |

(Continued)

*Primary Examiner* — Robert Long
(74) *Attorney, Agent, or Firm* — Steven A. Nielsen; www.NielsenPatents.com

(57) ABSTRACT

A surgical stapler includes a handle assembly 80 made of paper pulp products or other eco-friendly material. The handle assembly and components of the staple mechanism housing are designed to accommodate the decreased material strength of the handle assembly. Handle retainer ears 110 are attached to the staple mechanism housing and prevent flexing of the lever grip. The retainer ears in combination with a raised circular boss 16 of the handle assembly facilities the use of lower strength materials, such as paper pulp products. An efficient staple housing mechanism includes a new return spring 120, a visual guide rod or alignment indicator 150 and a flattened stapler guide 130. An improved lever grip includes concentrically trimmed arc in the lever grip sidewalls 117. An improved lever grip includes an extended arched rear section 113 to comport with a new positive mating area 115 of the handle.

18 Claims, 30 Drawing Sheets

Related U.S. Application Data is a continuation-in-part of application No. 13/626,269, filed on Sep. 25, 2012, now Pat. No. 9,226,749.

(51) Int. Cl.
    *A61B 17/29*     (2006.01)
    *A61B 90/00*     (2016.01)
    *A61B 50/36*     (2016.01)

(56) References Cited

U.S. PATENT DOCUMENTS

| | | | |
|---|---|---|---|
| 5,497,932 A * | 3/1996 | Brewer | B25C 5/11 227/132 |
| 7,793,812 B2 | 9/2010 | Moore et al. | |
| 2009/0206137 A1 | 8/2009 | Hall et al. | |
| 2010/0327042 A1 * | 12/2010 | Amid | A61B 17/0684 227/176.1 |
| 2014/0084041 A1 * | 3/2014 | Chase | A61B 17/0684 227/176.1 |
| 2014/0263560 A1 * | 9/2014 | Chase | A61B 17/0684 227/177.1 |

\* cited by examiner

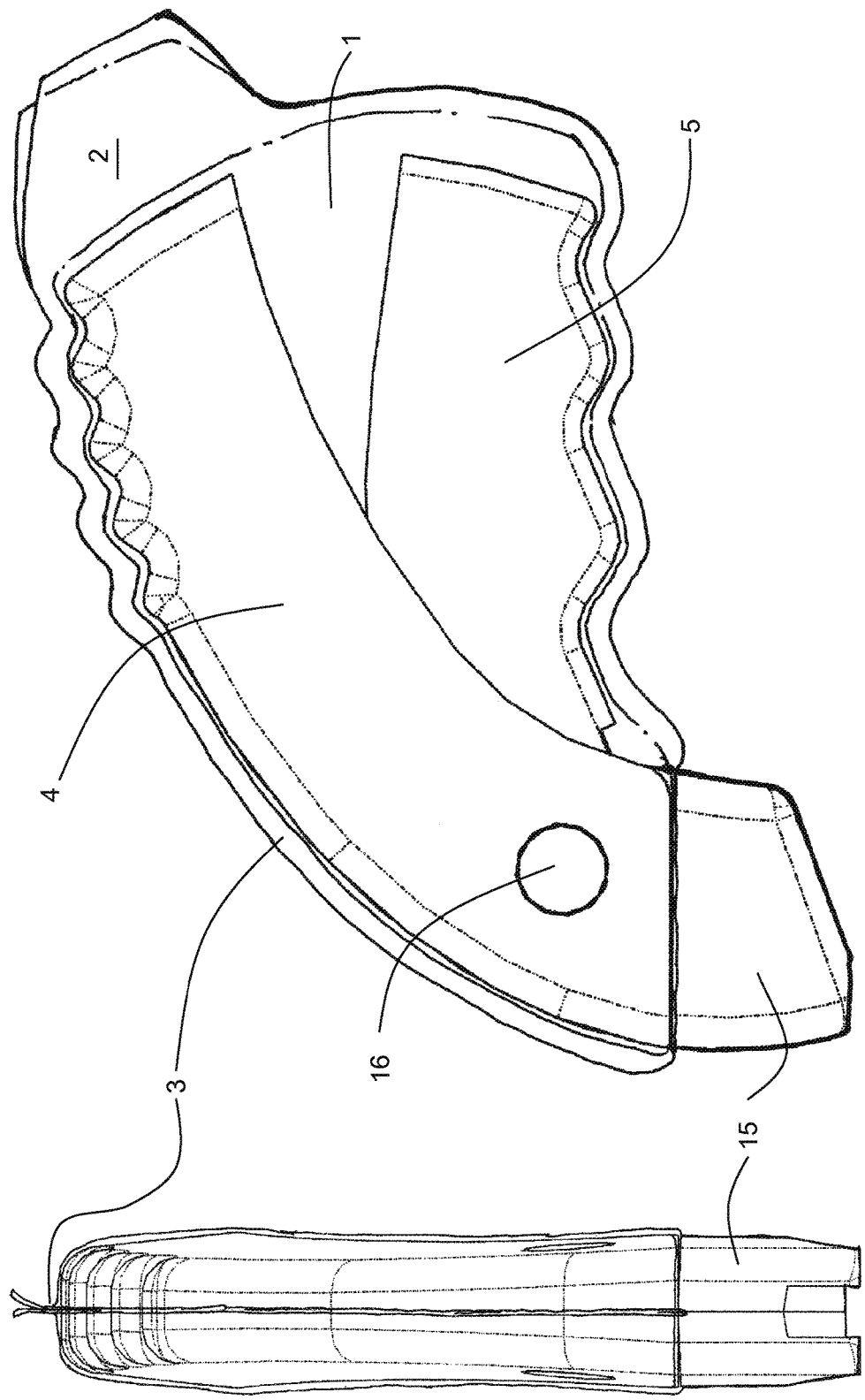
FIG. 1 FRONT VIEW
FIG. 2 SIDE VIEW

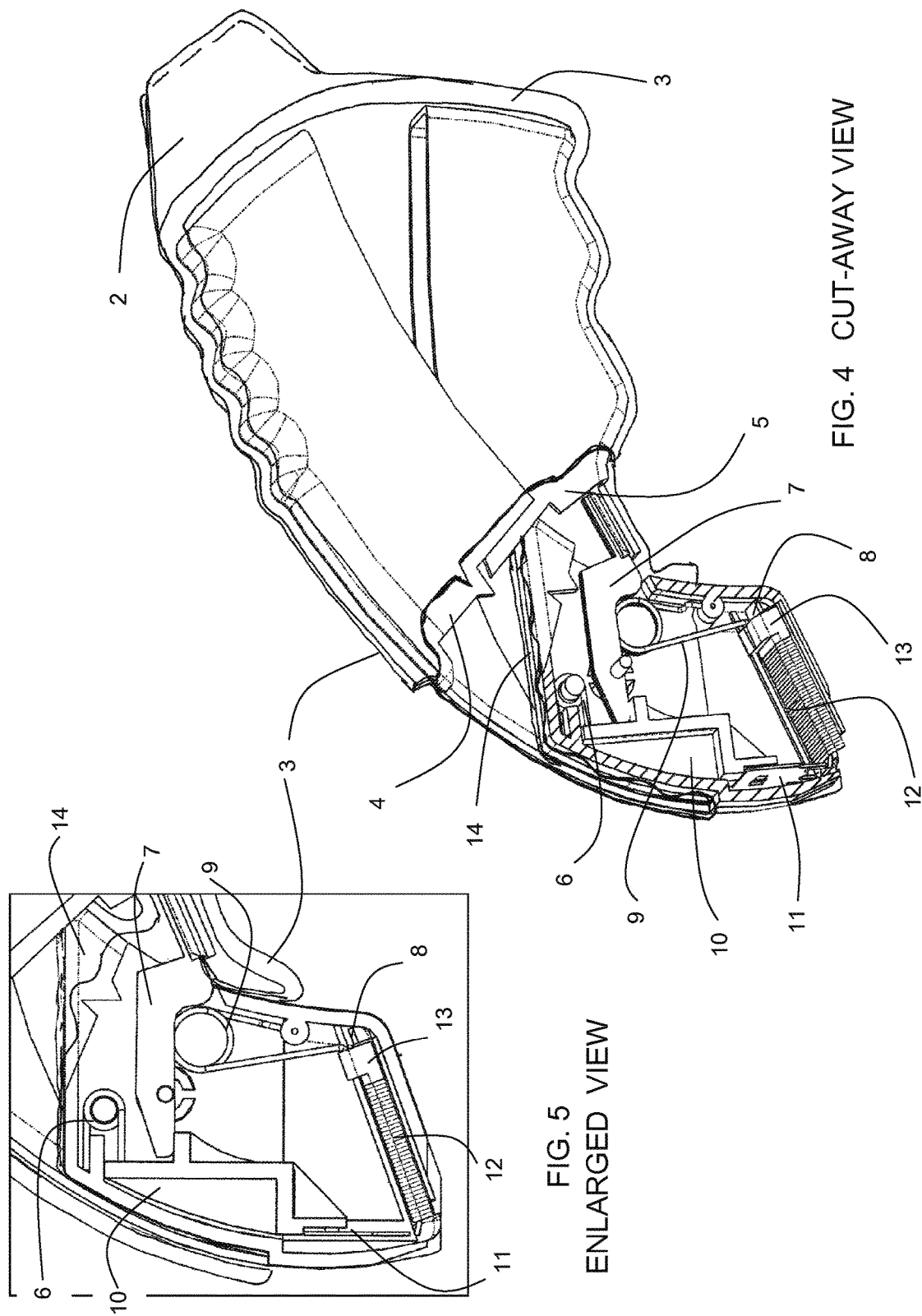

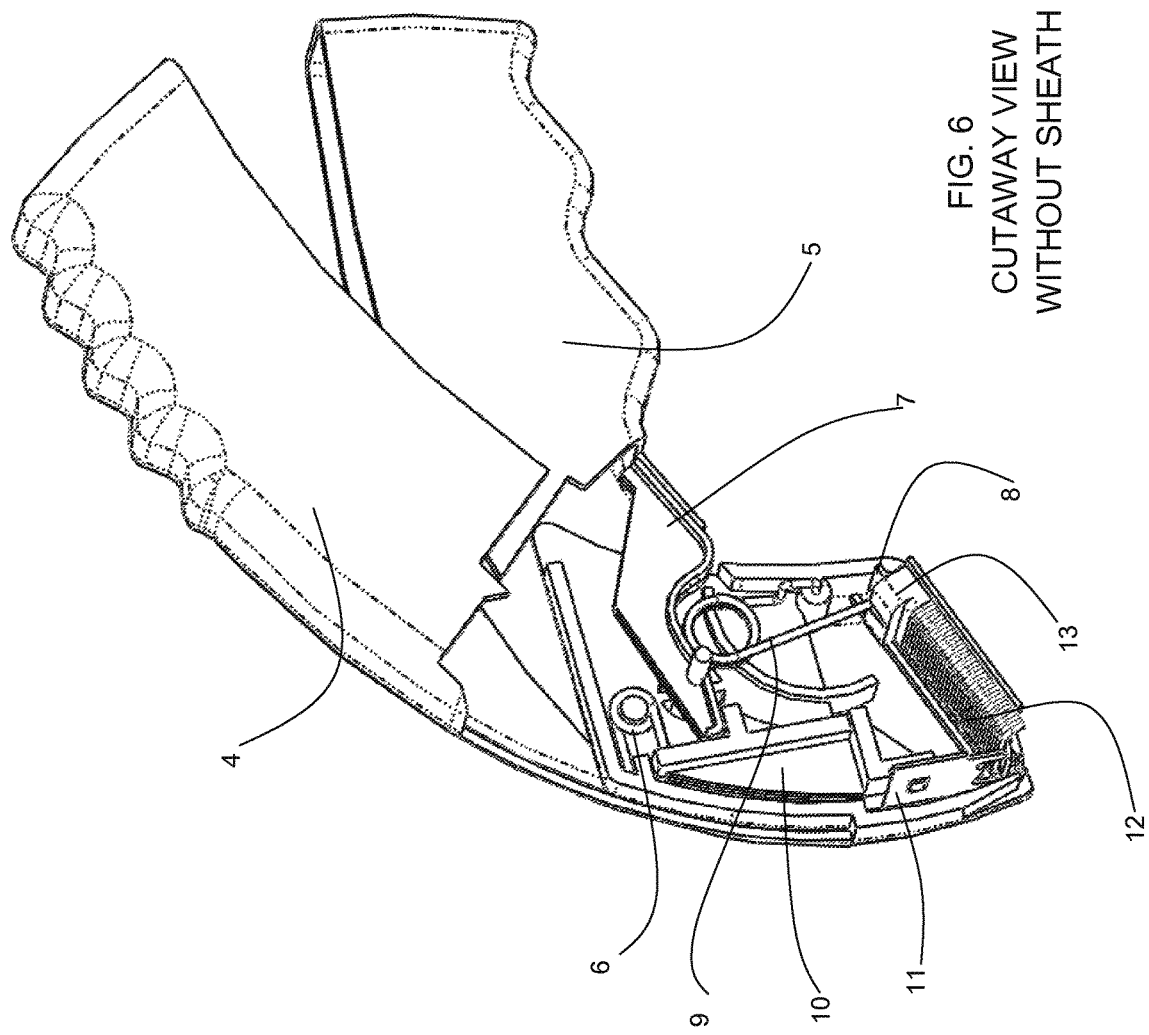

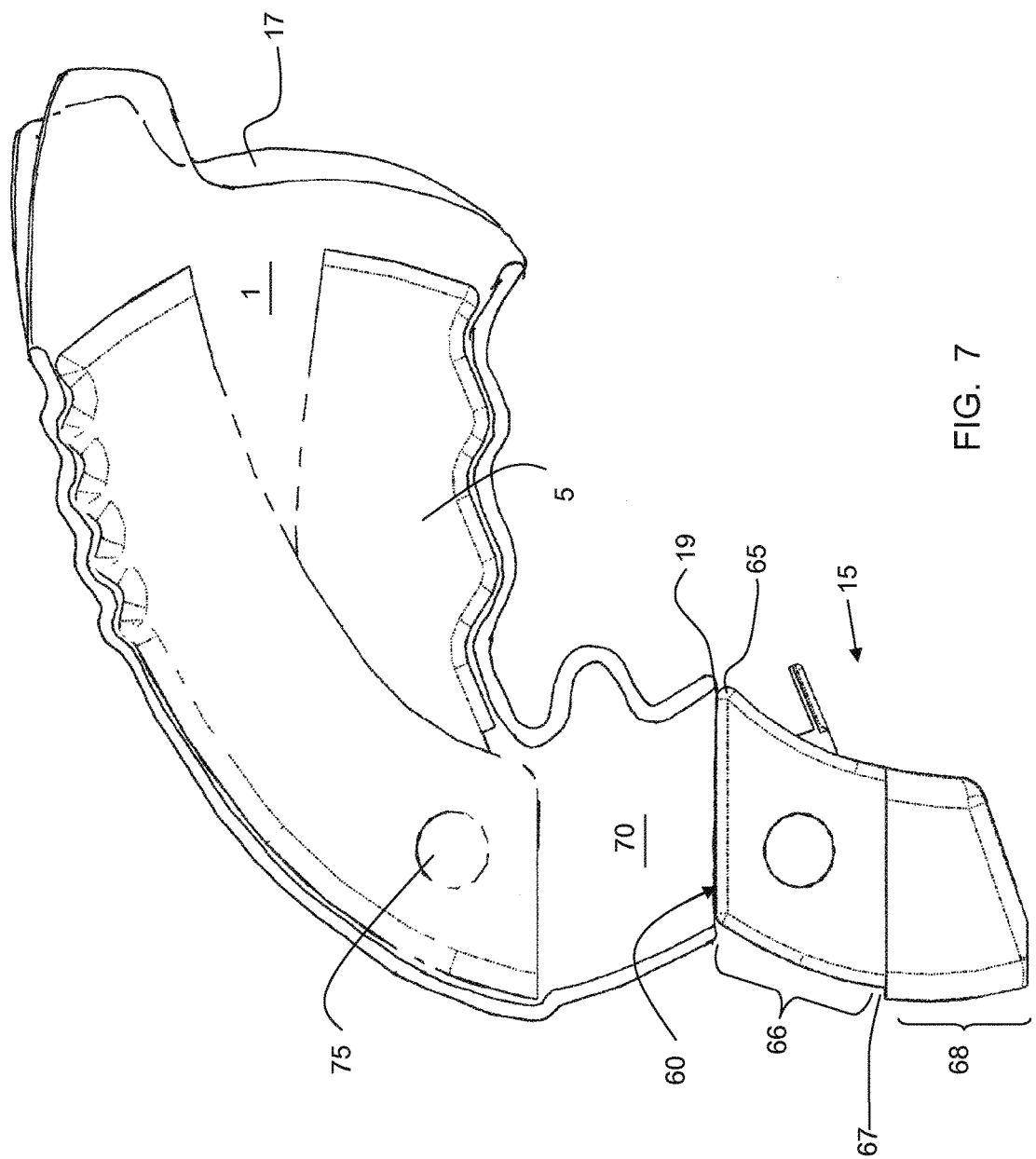

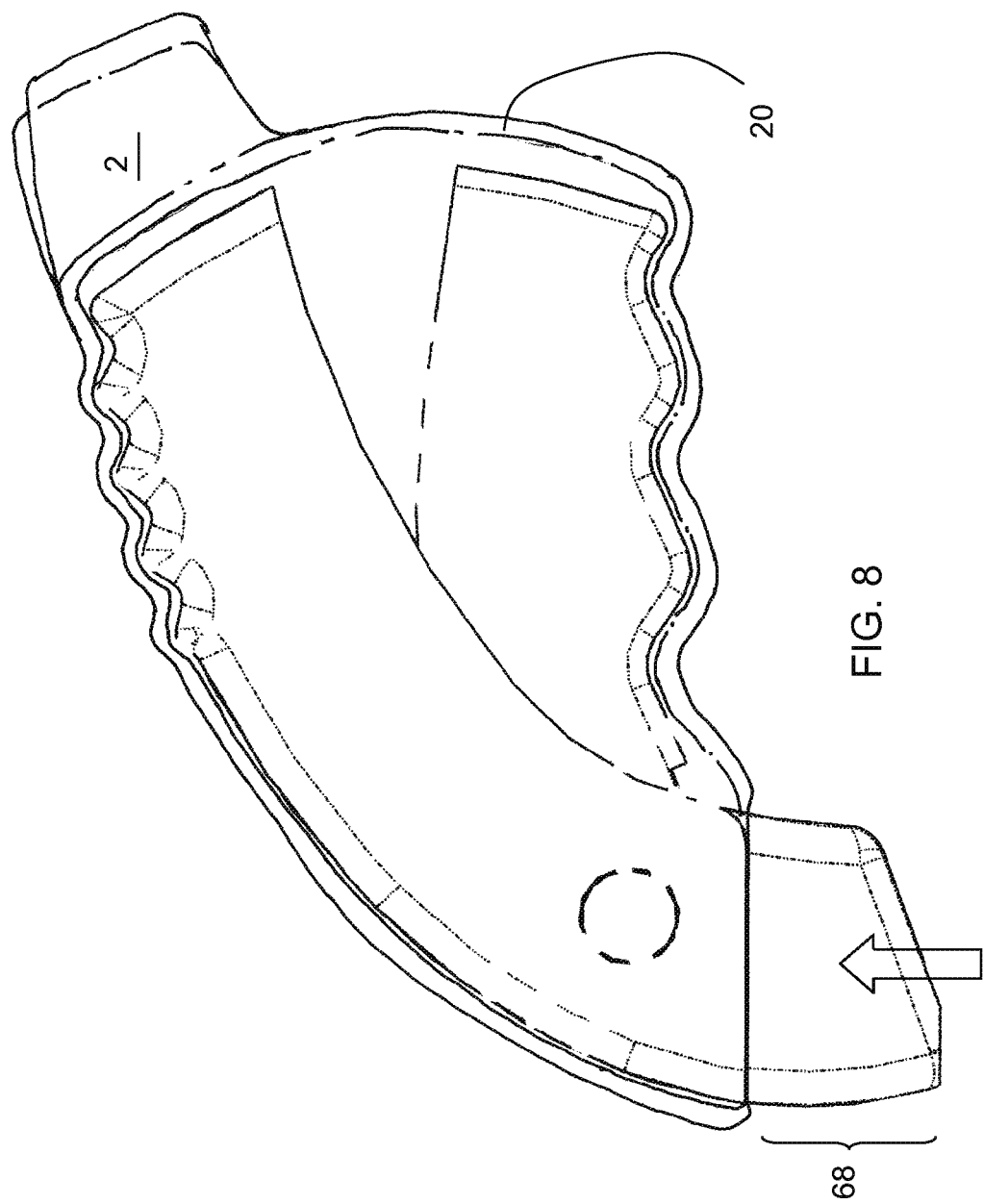

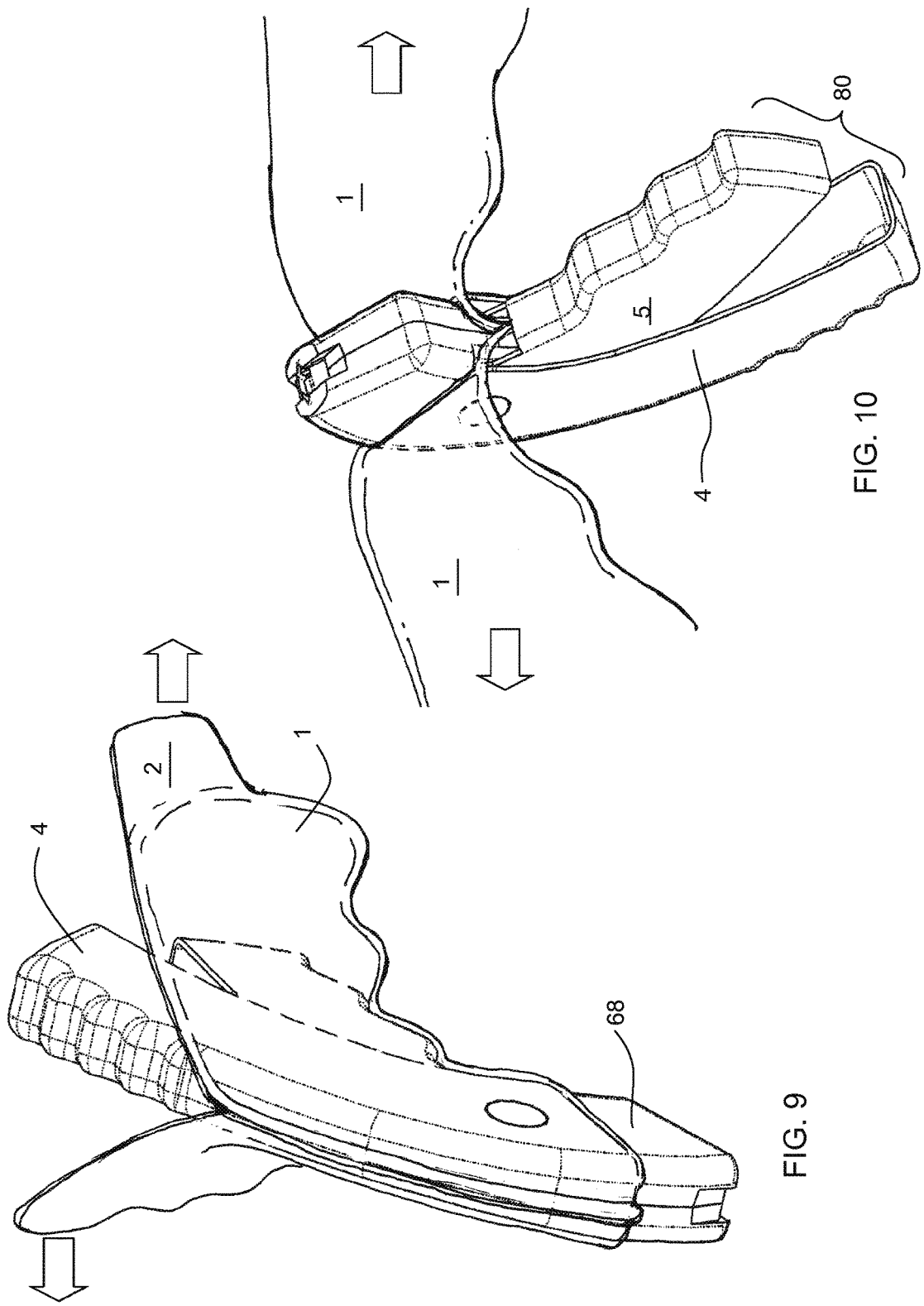

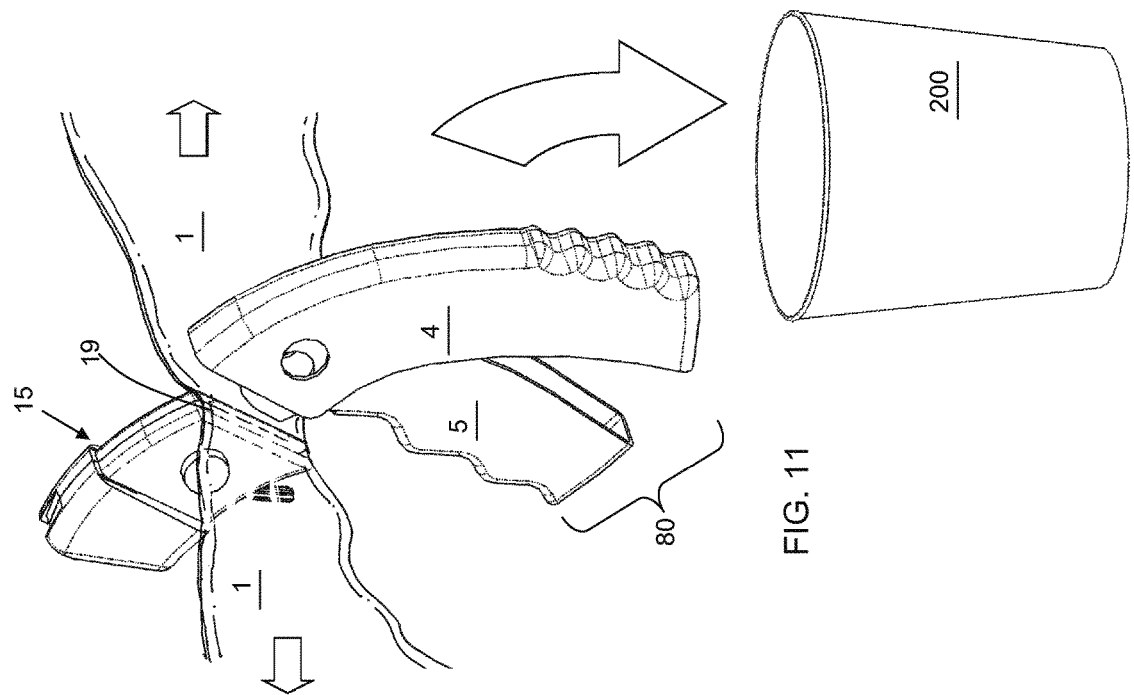

STAPLER MECHANISM ASSEMBLY

STAPLER HOUSING
DETAIL VIEW

ACTUATOR LEVER
DETAIL VIEW

STAPLE FOLDER BLOCK DETAIL VIEW

FIG. 18 STAPLE ADVANCE SPRING DETAIL VIEW

RETURN SPRING DETAIL VIEW

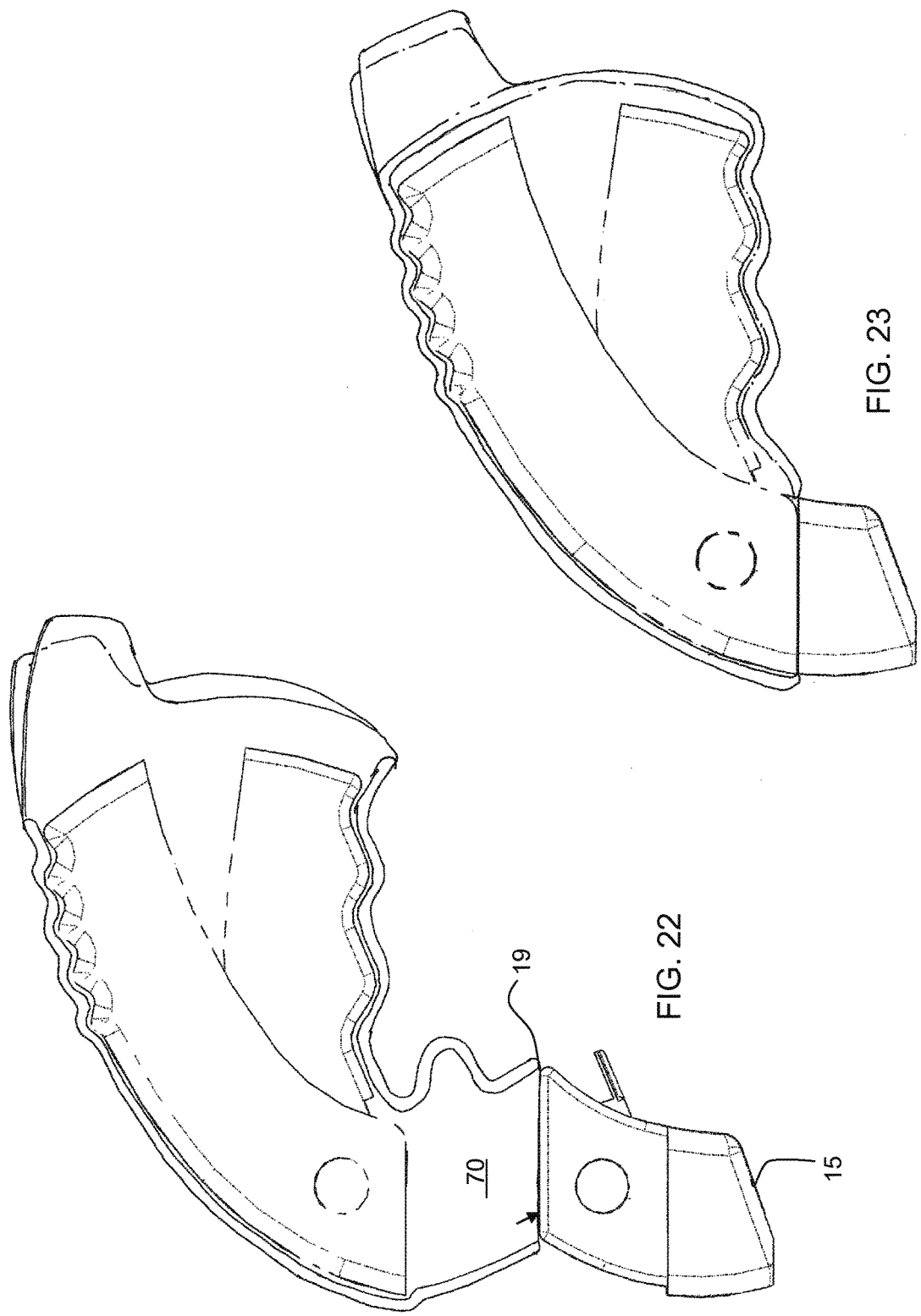

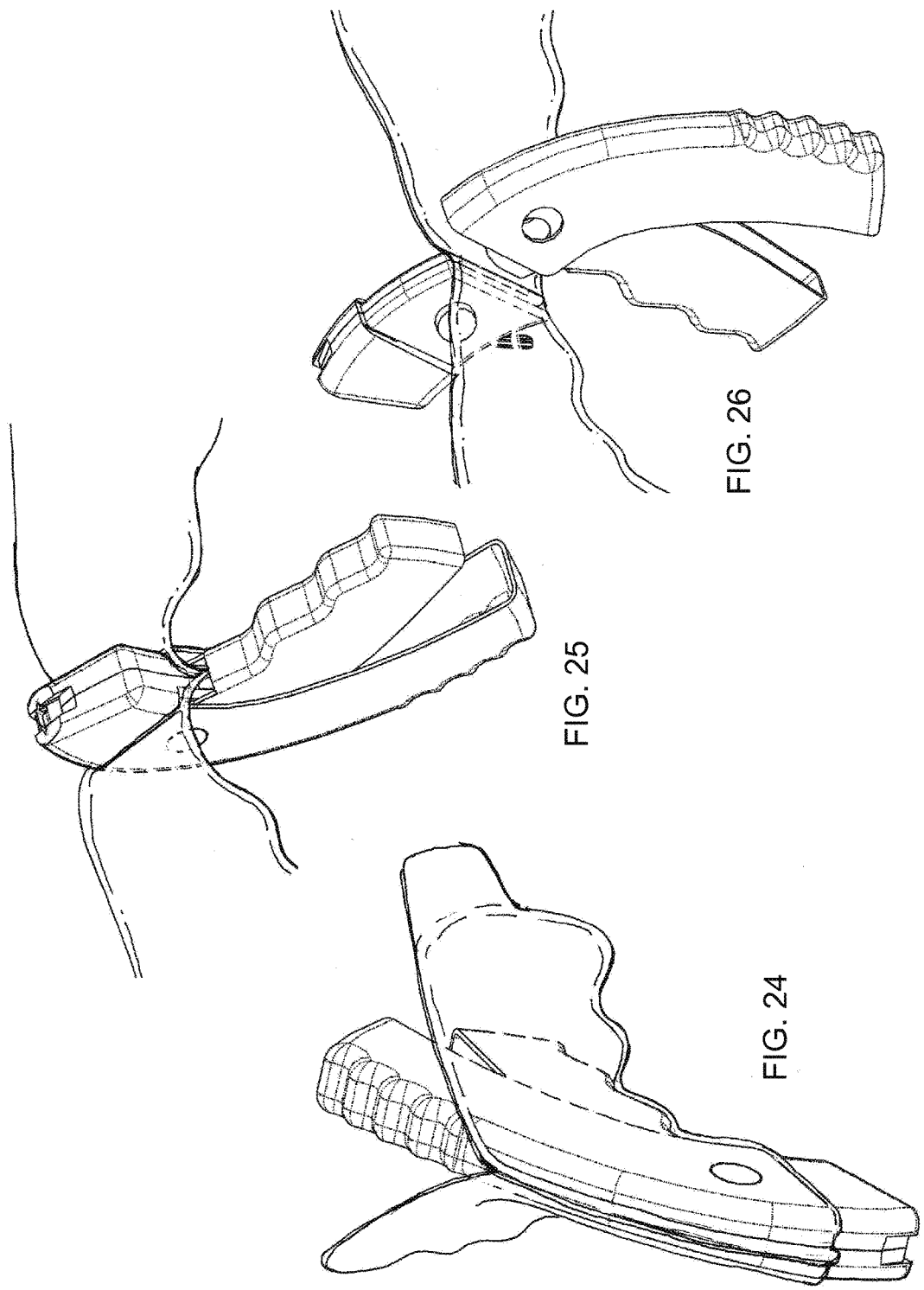

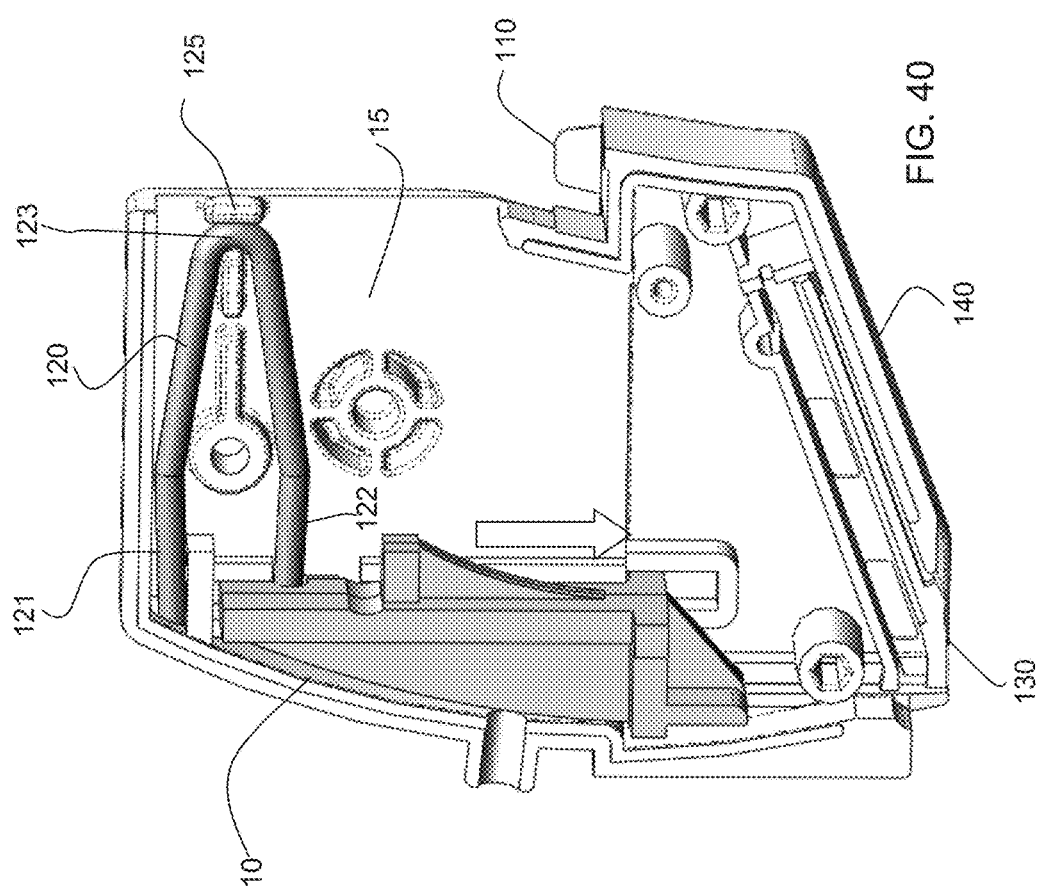

SKIN STAPLER WITH COMPONENTS OPTIMIZED FOR CONSTRUCTION WITH PLANT BASED MATERIALS

CROSS-REFERENCE TO RELATED APPLICATIONS

This application is a continuation in part of application Ser. No. 14/155,106 filed on Jan. 14, 2014 which is a continuation in part of application Ser. No. 13/626,269 filed on Sep. 25, 2012.

BACKGROUND OF THE INVENTION (1) Field of the Invention

The invention generally relates to disposable skin staplers. More particularly, the invention relates to means and methods of utilizing plant based materials while minimizing the use of petroleum based components.

(2) Description of the Related Art

Other disposable skin staplers are known in the related art. For example, U.S. Pat. No. 4,411,378 issued on Oct. 25, 1983 to Warman discloses the use of plastics in making a skin stapler. The use of plastics purportedly makes the Warman stapler disposable. Unfortunately, after just one use, the entire Warman stapler becomes a biohazard waste product requiring disposal by incineration.

U.S. Published Patent Application 2009/0206137 by Hall et al, published on Aug. 20, 2009 discloses a disposable loading unit for inserting staples into a traditional stapler. While the addition of staples to a stapler may prolong the useful life of a stapler, the Hall stapler appears to be devoid of any recyclable components and appears to undergo traditional sterilization procedures before each use.

U.S. Pat. No. 7,793,812 issued on Sep. 14, 2010 to Moore et al discloses a motor driven disposable loading unit for adding staples into a traditional stapler. No means or methods are disclosed to recycle parts of the Moore stapler in an environmentally sustainable manner.

BRIEF SUMMARY OF THE INVENTION

The present invention overcomes shortfalls in the related art by presenting an unobvious and unique combination and configuration of methods and components that prevent biohazard fouling of various stapler components. Embodiments of the present invention protect a handle and actuator grip from contamination and provide an integrated sheathing system to eject clean parts into a common recycling container intended for typical consumer paper products. After use, the disclosed handle assembly parts may be mixed with other consumer paper products for recycling. During use of a disclosed stapler, a protective sheathing keeps blood and other material away from the disclosed handle assembly. The disclosed handle assembly is artfully made from wood pulp products or other eco-friendly materials and hence is well suited for clean bin recycling. The construction of the disclosed handle assembly overcomes shortfalls in the related art wherein hard plastics have been used to achieve the necessary material strength.

After surgical use, tabs upon the disclosed sheath system are pulled, removing the sheathing from the handle assembly and ejecting the handle assembly into a recycling container, for clean-bin recycling.

The sheathing and sheathing tabs remain in the hands of the user. The sheathing remains attached to a staple mechanism housing. The user then drops the sheathing and attached staple mechanism housing into a biohazard container. Thus, the present invention overcomes shortfalls in the art by significantly reducing the volume of stapler components destined for a biohazard container.

In the known related art, entire stapling systems are subjected to biohazard exposure requiring entire systems to be incinerated, increasing pollution and the consumption of materials. In the prior art, the term "disposable" relates to the use of plastics that are inexpensive to produce. Unfortunately, the prior art fails to consider the elements of sustainability in the production and disposal of surgical staple systems.

Typically in a surgical environment, tools coming into direct contact with a patient are considered a biohazard and require 1.) expensive sterilization, a labor intensive process using copious amounts of hot water and cleaning chemicals or 2.) costly incineration, burning fuel and emitting harmful particulates into the air. The trend in the art is to use plastics to create one time use staplers and to incinerate such staplers after use. Thus, the prior art teaches away from the present embodiments and methods.

The prior art fails to teach, suggest or contemplate the disclosed use of sheathing material to protect stapler components or the construction of stapler components using wood pulp products. Disclosed embodiments present an unobvious integration of a sheathing material sealed onto and intertwined with stapler components.

Embodiments of the invention overcome shortfalls in the art by the careful engineering of protected components such that disclosed handles and actuator grips may be made from Molded Pulp Fiber (MPF) or other wood pulp products. The designs of the related art require the use of hard plastics to achieve the needed material strength for proper staple operation. The disclosed stapler mechanism designs overcome such prior art shortfalls.

The disclosed embodiments do not present a hardship or handicap to medical personal. The integrated sheathing system presents two tear tabs, that when pulled apart, eject the underlying and clean wood pulp components into clean bin recycle containers.

The disclosed embodiments include new staple mechanism housings, handle assemblies and other related components that require less force upon the disclosed handles and actuator grips, allowing for such components to be made of eco-friendly materials.

Disclosed embodiments may be constructed or used with or without a sheath. Disclosed embodiments solve long felt problems in the prior art by disclosing a new system wherein the positioning of a raised circular boss is aligned with the pivot point of the actuator lever. The further use of a support shelf integrated into a mechanism housing provides the required configuration and mechanical support to allow for the use of plant based and other ecofriendly materials as described herein.

The disclosed raised circular boss solves several problems of the prior art by efficiently enabling the use of MPF and similar materials. In the prior art, injection molded ABS is the industry standard but fails to be ecologically efficient. ABS is an order of magnitude stronger than MPF, hence the disclosed embodiments suitable for use with MPF are a radically departure from the prior art.

Economical MPF production process is limited to a 1 mm thickness (compared with 2.2 mm for ABS), and fails to provide high-strength material properties needed for ribs, bosses, and actuator levers that can be attained with ABS.

The force needed to fold a staple is quite high, necessitating the need to spread the force out over a large enough area to allow 35 staples to be formed without deforming the MPF parts. This includes the handle, which needs to be held securely in position, and the lever grip, which must pivot around the axis of the stapler mechanism, while moving the internal actuator lever a precise distance with-out deforming enough to prevent a failure of the staple forming process.

After many concepts were developed and tested, it was discovered that positioning a raised circular boss on either side of the mechanism housing, and aligned with the pivot point of the mechanism's actuator lever, in combination with a support shelf on the mechanism housing, would give the required support and accuracy to meet the requirements of the disclosed embodiments.

Since the handle needs to be securely fixed in position while the lever grip rotates freely around a specific axis, the prior art's use positioning pins, clips, or screws does not work, and would impede the motion of the lever grip.

A new handle retainer clip prevents the disclosed handles from deforming or detaching from the circular boss and support shelf.

The disclosed retainer clip in combination with the raised circular boss provides unexpectedly excellent results in allowing for the use of lightweight recyclable materials such as MPF which has far less material strength as compared to the plastics used in the prior art. The raised circular boss in combination with the retainer clip discussed below, overcomes shortfalls in the art by efficiently facilitating the use of MPF and other recyclable materials Excessive conceptualization and experimentation was required to reduce to practice the disclosed retainer clip and related assemblies. The new retainer clip provides the unexpected result of securely positioning the handle in position during operation and yet, in the case of use with a removable sterile sheath, flexes out of the way to allow the sheath, handle, and lever grip to be easily removed from the mechanism housing assembly.

In the best mode known to date, the preferred embodiment uses neither a sheath nor a retainer clip. The retainer clip is replaced with handle retainer ears. The handle retainer ears have utility subtle and unsubtle. The retainer ears reduce deflection of the MPF handle and related MPF parts, thus increasing the use of MPF. The retainer ears may be positioned posterior to the handle pivot boss to better retain the MPF handle. The replacement of the retainer clip with the handle retainer ears greatly reduces the amount of plastic of the product and reduces the number of detachable parts.

In the best mode known to date, a new handle alignment pin accommodates for the low strength of the MPF handle. The new handle alignment pin assists in reducing handle rotation around the handle pivot boss.

In the best mode known to date, an improved lever grip features an extended posterior protrusion that extends to, or extends past the posterior section of the handle. The artful combination of the extended posterior protrusion of the lever grip and shorter posterior section of the handle creates a positive lever grip stop against the handle. This configuration keeps the stresses of the MPF parts within their material limits. The disclosed stop configuration comprises the rear or posterior sections of the lever and handle where the MPF parts are relatively stronger due to the arches or curvatures of the rear sections. In particular, the lever section stop area is strengthened by the disclosed arch configuration.

In the best mode known to date, the anterior or front section of the lever grip sidewalls features concentrically shaped edges that comport to the radius of the pivot boss. The concentric section of the lever grip sidewalls assists in more evenly dissipating the forces exerted upon the lever grip. Such dissipation of forces helps to make the use of MPF in the lever grip possible. The disclosed lever grip sidewalls keep the forces exerted upon the MPF lever grip well within material limitations.

In the best mode known to date, an improved return spring features a resilient member or spring with two legs and a center retention area. The center retention area may be secured by a spring locating boss. The improved return spring is extended by the travel of the folder block. The unique configuration of the disclosed return spring allows for the full travel and return of the folder block without the return spring being fouled, impeded or disturbed by adjacent components.

In the best mode known to date, an improved staple mechanism housing features a flattened stapler guide that rests positively upon a patient to achieve a perpendicular or normal angle of staple insertion. The stapler guide is adjacent to a lower edge section that is angled upwardly from the stapler guide. This upward angle is helpful in keeping the majority of the staple mechanism housing off of the patient. The angle between the stapler guide and the lower edge section may be in the range of 10 to 30 degrees.

In the best mode known to date, a new alignment indicator is attached or formed into the staple mechanism housing. The alignment indicator assists in providing a visual reference to keep the stapler at the correct angle while in use.

These and other objects and advantages will be made apparent when considering the following detailed specification when taken in conjunction with the drawings.

BRIEF DESCRIPTION OF THE DRAWINGS

FIG. 1 depicts a front view of a disclosed surgical stapler

FIG. 2 depicts a side view of a disclosed surgical stapler

FIG. 4 depicts a side view and cutaway view of a disclosed surgical stapler

FIG. 5 depicts an expanded view of various stapler components

FIG. 6 depicts a sectional view of a disclosed surgical stapler without a sheath FIG. 7 depicts a disclosed surgical stapler in a state of partial assembly FIG. 8 depicts a disclosed surgical stapler in a state of near assembly FIG. 9 depicts a sheath being separated from a handle assembly FIG. 10 depicts a sheath in a further state of separation FIG. 11 depicts a handle and actuator grip level being separated from a staple mechanism housing FIG. 22 depicts a staple mechanism housing in connection with a sheath FIG. 23 depicts an assembled surgical stapler with sheath attached FIGS. 24 to 26 depict a disassembly procedure of a surgical stapler FIG. 40 depicts a plan view of a new return spring

Figure 3:
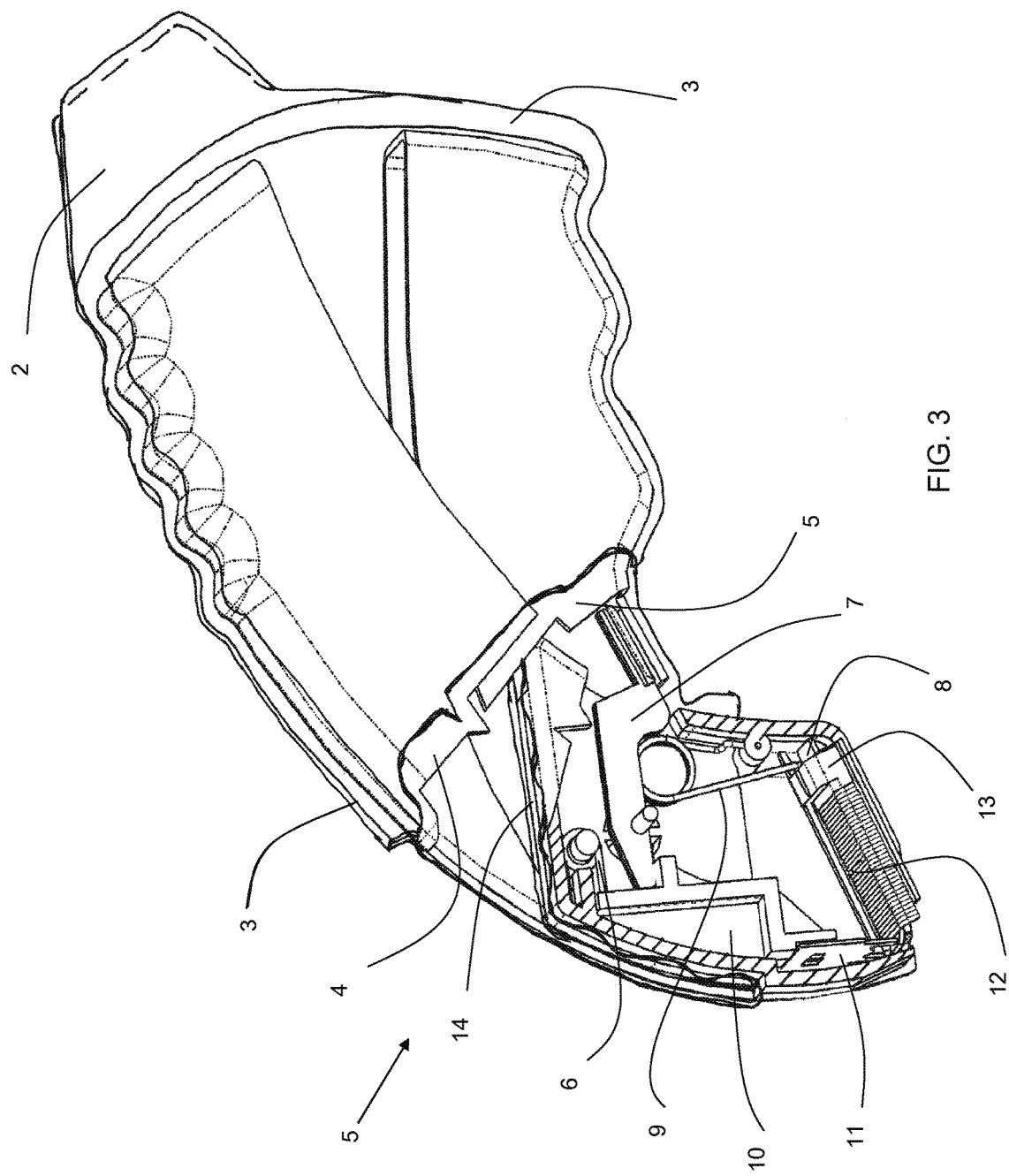
FIG. 3 depicts a side view and cutaway view of a disclosed surgical stapler

REFERENCE NUMERALS IN THE DRAWINGS 1 sheath
2 grip tabs attached to the sheath 1, used to open sheath at proximal side
3 seam on sheath, seam tears apart as part of disposal process
4 handle, accepts actuator grip 5 and staple mechanism housing
5 actuator grip lever, sometimes made of Molded Pulp Fiber or MPF
6 return spring or staple folder
7 actuator lever, sometimes made of molded plastic
8 staple carrier tray, sometimes made from a stamped stainless steel sheet
9 staple advance spring, sometimes made of stainless steel wire
10 staple folder block, sometimes made of molded plastic
11 staple folder plate, sometimes made of stamped stainless steel
12 staple stack, comprised of a plurality of staples
13 staple advance block, sometimes made of molded plastic
14 section of sheath folded inside handle and actuator grip lever
15 staple mechanism housing, comprised of a right 15R side and left side15L, sometimes made of molded plastic
15R right side of staple mechanism housing 15
15L left side of staple mechanism housing 15
16 handle pivot boss, mates with round void 75 of handle and void 76 of actuator grip
17 sheath with sides sealed and back open for handle insertion
19 attachment between sheath and stapler mechanism assembly which may be accomplished with various means such as adhesive bonding, ultrasonic welding or mechanical fastening
20 sheath in a final seal configuration after staple mechanism housing 15 is inserted into a handle assembly 80
22 distal section of actuator lever arm, extends from staple mechanism housing and is rotated by a pivoting actuator grip handle to fold staples
23 recessed view area of staple mechanism housing 15, allowing a surgeon a clear view of the stapling process and clearance for everted tissue to be stapled
24 boss of staple mechanism housing 15, used with return spring 6
25 curved rib of staple mechanism housing 15, used to center staple advance spring 9 within staple mechanism housing 15
26 pivot void found within staple mechanism housing 15 positioned to allow the staple advance spring 9 to clear all internal parts and to apply even pressure throughout travel
27 recess within staple mechanism housing 15, for staple carrier tray 8, used to properly position staples
28 track within staple mechanism housing 15, used for staple folder plate 11
29 front inside wall of staple mechanism housing 15, used to retain a staple during forming without allowing staples to jam due to multiple staple feed
30 vertical track within staple mechanism housing 15, used for staple folder block 10
31 pivot void found within staple mechanism housing 15, used for actuator lever 7
32 rib of actuator lever 7, contoured to clear other internal components throughout movement
33 pivot pin of actuator lever, rotates in the pivot void 31 of the staple mechanism housing 15
34 block contact area of actuator lever 7, used for a smooth interface with staple folder block 10
35 wide rib of actuator lever 7, provides rigidity to actuator lever and distributes actuating force from actuator grip lever 5
36 vertical rib of staple folder block 10, runs in vertical track 30 of staple mechanism housing 15
37 protruding surface of staple folder block 10, mates with actuator lever 7
38 ribs or curved ribs of staple folder block 10, used for more even transfer of forces to staple folder plate 11
39 recessed area of staple folder block 10, used for staple folder plate 11
40 raised block of staple folder block 10, mates with void within staple folder plate 11
41 pivot leg of staple advance spring 9, mates with void of staple mechanism housing 15
42 offset of staple advance spring 9, centers the staple advance spring 9 within the staple mechanism housing 15
43 triple loop of staple advance spring 9, retains the staple advance spring 9 within limits of intended elasticity
44 pusher leg of staple advance spring 9, rotates around triple loop 43 to advance staples
45 leg of staple advance spring 9, mates with staple advance block 13
46 double loop of return spring 6, keeps the return spring 6 within limits of intended elasticity
47 legs of return spring 6, urge a staple folder block 10 to a starting position
48 voids within in staple mechanism housing 15, used to view the remaining quantity of staples
50 void within staple folder plate 11, used to mate with staple folder block
60 folded edge of sheath 1
65 superior side of staple mechanism housing 15, the superior side used as an attachment point 19 for the folded edge 60 of a sheath 66 narrow section of staple mechanism housing 15, fits into inferior openings within the handle assembly 80
67 lateral ledge of staple housing mechanism 15
68 base section of staple mechanism housing 15
70 loose section of sheath 1 for placement within handle assembly 80
75 center void within handle 4, used to mate with boss 16
76 center void within actuator grip lever, used to mate with boss 21
77 interior void within handle 4, the interior void defined by a plurality of exterior handle walls
80 handle assembly, comprising a handle 4 and actuator grip lever 5
81 handle retainer
82 assembly ribs with interference fit ribs 96
83 assembly voids to accept assembly ribs 82
84 proximal configuration of MPF handle from raised circular boss center
85 distal configuration of MPF handle from raised circular boss center
86 staple carrier assembly fixture pin
87 locator void of staple carrier assembly fixture pin
89 center point of raised circular boss 16
96 interference fit rib of assembly rib 82
97 upper shelf of assembly rib 82
98 distal surface of handle retainer
99 distal surface of an assembly rib 82
100 a disclosed surgical stapler in general
105 handle alignment pin
110 handle retainer ear
112 positive mating area of the rear section of the lever grip 4
113 arched rear section of the lever grip 4
115 positive mating area of the rear section of the handle 5
117 lever grip sidewalls
118 concentrically trimmed arc of lever grip sidewalls
120 return spring
121 upper leg of return spring 120
122 lower leg of return spring 120
125 spring locating boss
130 flattened stapler guide, stapler guide or staple guide of staple mechanism housing
135 angle between flattened stapler guide 130 and lower edge section 140 of the staple mechanism housing
140 rear lower edge section of the staple mechanism housing
150 alignment indicator or alignment indicator of the staple mechanism housing
151 lower horizontal section of the alignment indicator 150
152 front vertical section of the alignment indicator 150
200 clean waste recycle bin

DETAILED DESCRIPTION OF EMBODIMENTS OF THE INVENTION

The following detailed description is directed to certain specific embodiments of the invention. However, the invention can be embodied in a multitude of different ways as defined and covered by the claims and their equivalents. In this description, reference is made to the drawings wherein like parts are designated with like numerals throughout.

Unless otherwise noted in this specification or in the claims, all of the terms used in the specification and the claims will have the meanings normally ascribed to these terms by workers in the art.

Unless the context clearly requires otherwise, throughout the description and the claims, the words "comprise," "comprising" and the like are to be construed in an inclusive sense as opposed to an exclusive or exhaustive sense; that is to say, in a sense of "including, but not limited to." Words using the singular or plural number also include the plural or singular number, respectively. Additionally, the words "herein," "above," "below," and words of similar import, when used in this application, shall refer to this application as a whole and not to any particular portions of this application.

The above detailed description of embodiments of the invention is not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. For example, while steps are presented in a given order, alternative embodiments may perform routines having steps in a different order. The teachings of the invention provided herein can be applied to other systems, not only the systems described herein. The various embodiments described herein can be combined to provide further embodiments. These and other changes can be made to the invention in light of the detailed description.

Any and all the above references and U.S. patents and applications are incorporated herein by reference. Aspects of the invention can be modified, if necessary, to employ the systems, functions and concepts of the various patents and applications described above to provide yet further embodiments of the invention.

These and other changes can be made to the invention in light of the above detailed description. In general, the terms used in the following claims, should not be construed to limit the invention to the specific embodiments disclosed in the specification, unless the above detailed description explicitly defines.

FIG. 1 depicts a front view with a stapler mechanism housing 15 and a seal seam 3.

FIG. 2 depicts a side view of a stapler having a handle 4, sometimes made of molded Pulp Fiber (MPF) or other wood pulp product, a handle pivot boss 16, a sheath 1, with the sheath having a pair of grip tabs 3.

FIG. 3 depicts a sectional view showing sheath tab 2, various sections of seal seams 3 as well various components within the staple mechanism housing 15. The staple mechanism housing includes a staple stack 12, a staple advance block 13, a staple carrier tray 8, an actuator lever 7, a return spring 6, a staple advance spring 9, a staple folder plate 11, and a stapler folder block 10.

FIG. 4 depicts a sectional view as in FIG. 3 and is used as a reference for FIG. 5. FIG. 5 depicts views of a return spring 6, an actuator lever 7, a staple carrier tray 8, a staple advance spring 9, a staple folder block 10, a staple folder plate 11, a staple stack 12 or stack of staples, a staple advance block 13, and a sheath section 14 folded inside a handle 4.

FIG. 6 depicts an embodiment before a sheath is applied and shows a handle 4 superior to an actuator grip lever. FIG. 6 further depicts a return spring 6, an actuator lever 7, a staple carrier tray 8, a staple advance spring 9, a staple folder block 10, a staple folder plate 11, a staple stack 12 or stack of staples and a staple advance block 13.

FIG. 7 depicts a sheath 1 with sides sealed with an open back section 17. When the sheath is in an open position 17, a handle and actuator grip may be inserted into the sheath.

A folded edge 60 of the sheath is shown in attachment 19 with the superior side 65 of a staple mechanism housing 15.

In FIG. 7, the sheath includes a loose section 70 which folds over a narrow section 66 of the staple mechanism housing during the insertion process.

FIG. 8 depicts a staple mechanism housing inserted into a handle assembly. The sheath protrudes from the void 75 of the handle and the sheath covers the boss of the staple mechanism housing. A base section 68 of the staple mechanism housing is left exposed. The sheath is shown in a condition 20 wherein the sheath is in a final seal configuration after the staple mechanism housing is inserted into the handle assembly.

FIG. 9 depicts a sheath with tabs 2 being pulled outwardly, and exposing the handle 4.

FIG. 10 depicts a sheath that is flexed at or near a lateral ledge of staple mechanism housing. The sheath is shown to have cleared the handle assembly 80. The pulling of the sheath is just starting to separate the handle assembly from the staple mechanism housing.

FIG. 11 depicts a separated handle 4 and actuator grip lever 4 falling into a clean waste recycle bin 200. The sheath 1 is shown secured at an attachment point 19 or attachment line found upon a superior side of the staple mechanism housing.

Figure 12:
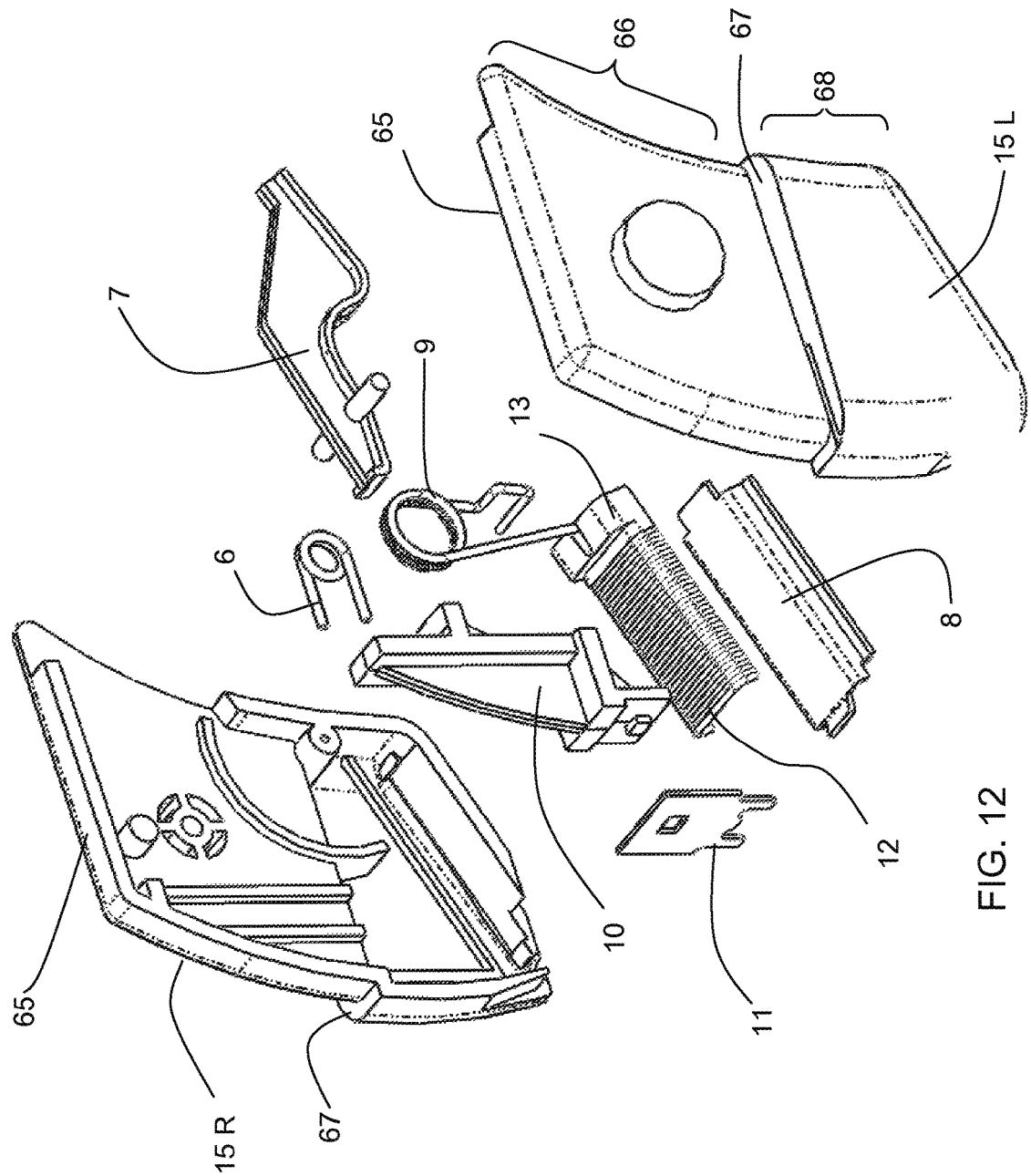
FIG. 12 depicts an exploded view of a staple mechanism housing

FIG. 12 depicts an exploded view of a staple mechanism housing comprising a right side 15R, left side 15L, a return spring 6, actuator lever 7, staple carrier tray 8, staple advance spring 9, staple folder block 10, staple folder plate 11, a staple stack 12 and a staple advance block 13. The left side 15 L of the staple mechanism housing is shown with a superior side 65 which is sometimes used as a point or line of attachment 19 to secure a sheath. A narrow section 66 is found upon a superior end of the left side 15L component, the narrow section fits into an end of the handle assembly. A lateral ledge 67 stops the staple mechanism housing from further insertion into the handle assembly.

Figure 13:
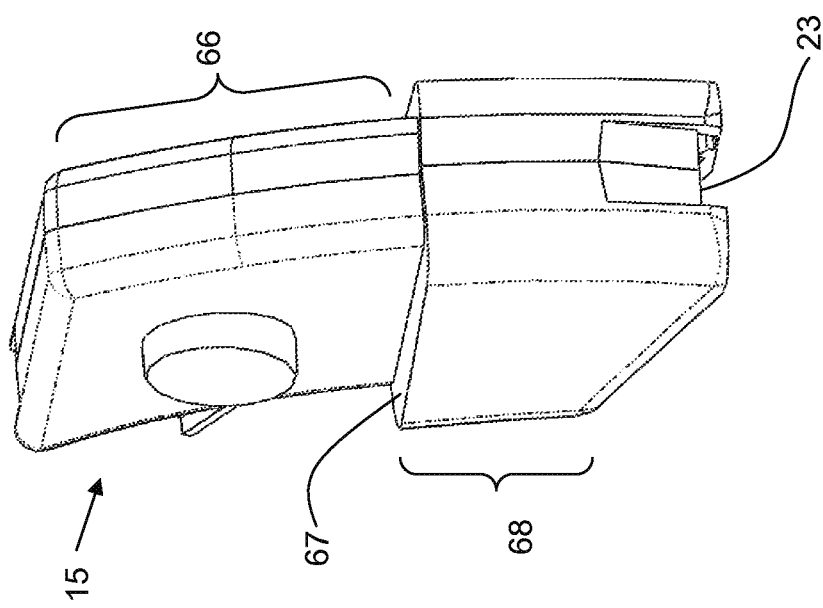
FIG. 13 depicts a front perspective view of a staple mechanism housing

FIG. 13 depicts an assembled staple mechanism housing 15 having a narrow section 66, three lateral ledges 67, a base section 68 and a recessed view area sometimes used by an end user for clear view of the stapling process and for clearance of everted tissue to be stapled.

Figure 14:
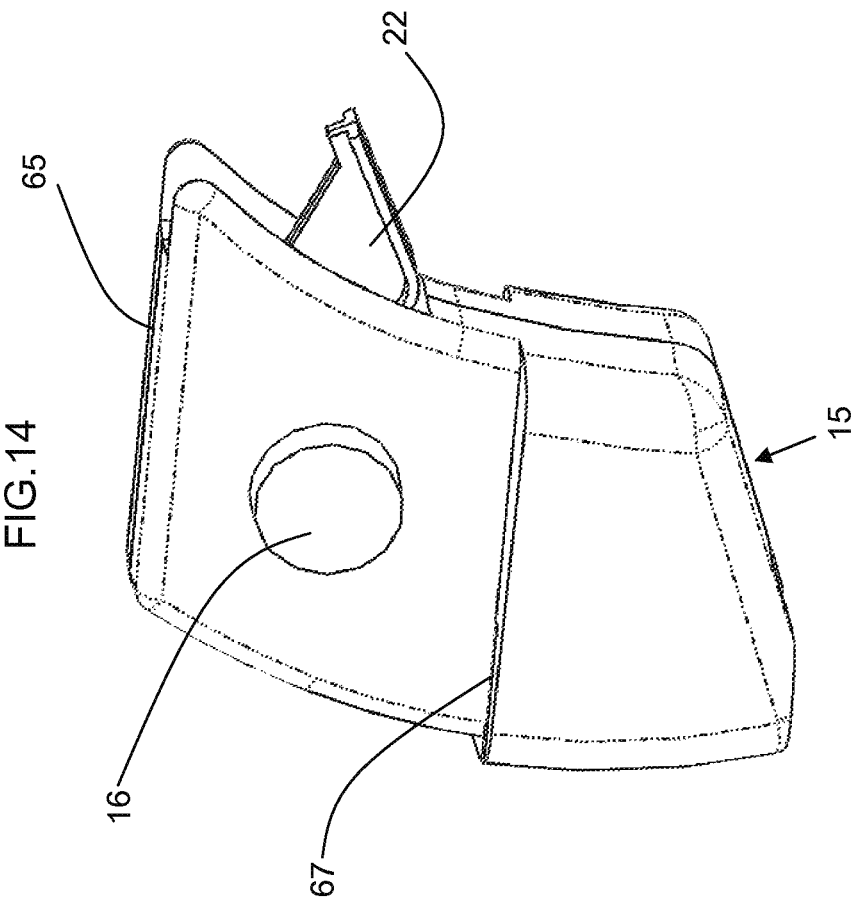
FIG. 14 depicts a side view of a staple mechanism housing

FIG. 14 depicts a side view of a an assembled staple mechanism housing 15 having a handle pivot boss 16, superior side 65, three lateral ledges 67 and a distal section 22 of actuator lever arm, extends from staple mechanism housing and is rotated by a pivoting actuator grip handle to fold staples.

Figure 15:
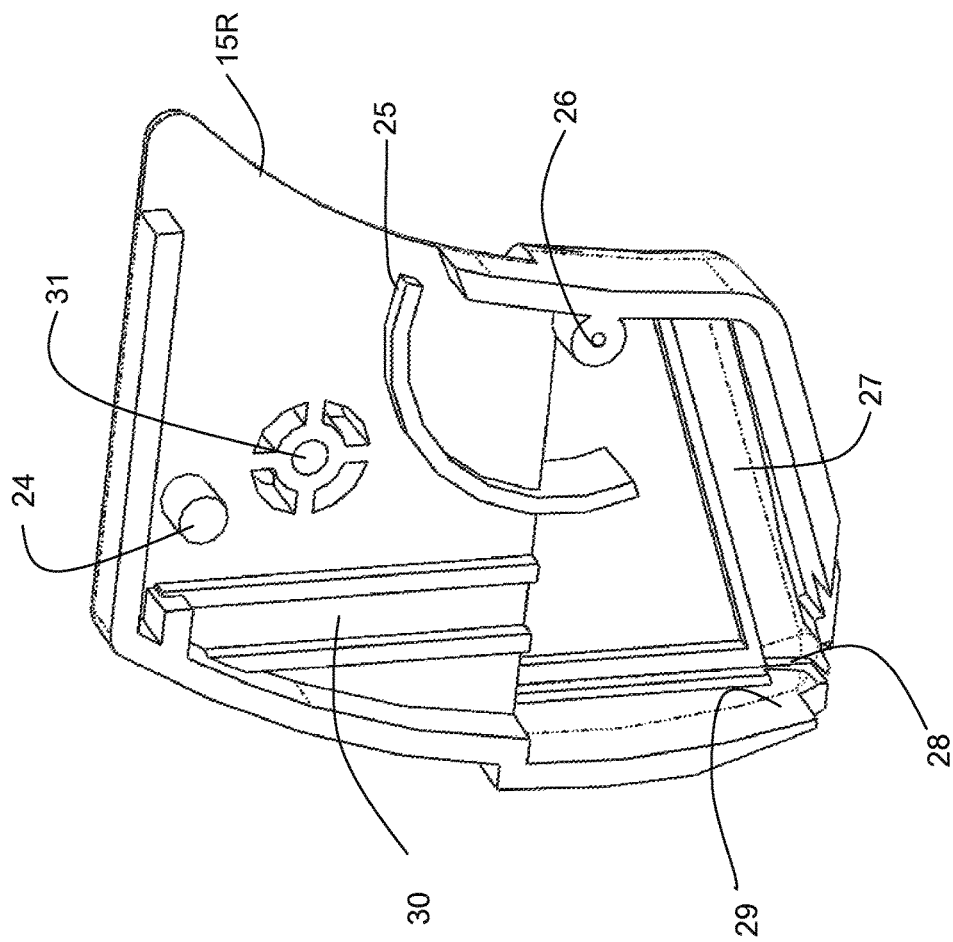
FIG. 15 depicts a sectional view of a staple mechanism housing

FIG. 15 depicts a right side 15R of a staple mechanism housing comprising a boss 24 used with a return spring 6, a curved rib 25 used to center staple advance spring 9 within a staple mechanism housing, a pivot void 26 positioned to allow the staple advance spring 9 to clear all internal parts and to apply even pressure throughout travel of the actuator lever 7. FIG. 15 also depicts a recess 27 for use with a staple carrier tray 8, used to properly position staples. A track 28 is used to guide a staple folder plate 11. A front inside wall 29 may be used to retain a staple during forming without allowing staples to jam due to multiple staple feed. A vertical track 30 is sometimes used with a staple folder block 10. A pivot void 31 is defined by a vertical wall of staple mechanism housing, the pivot void sometimes used by a actuator lever 7.

Figure 16:
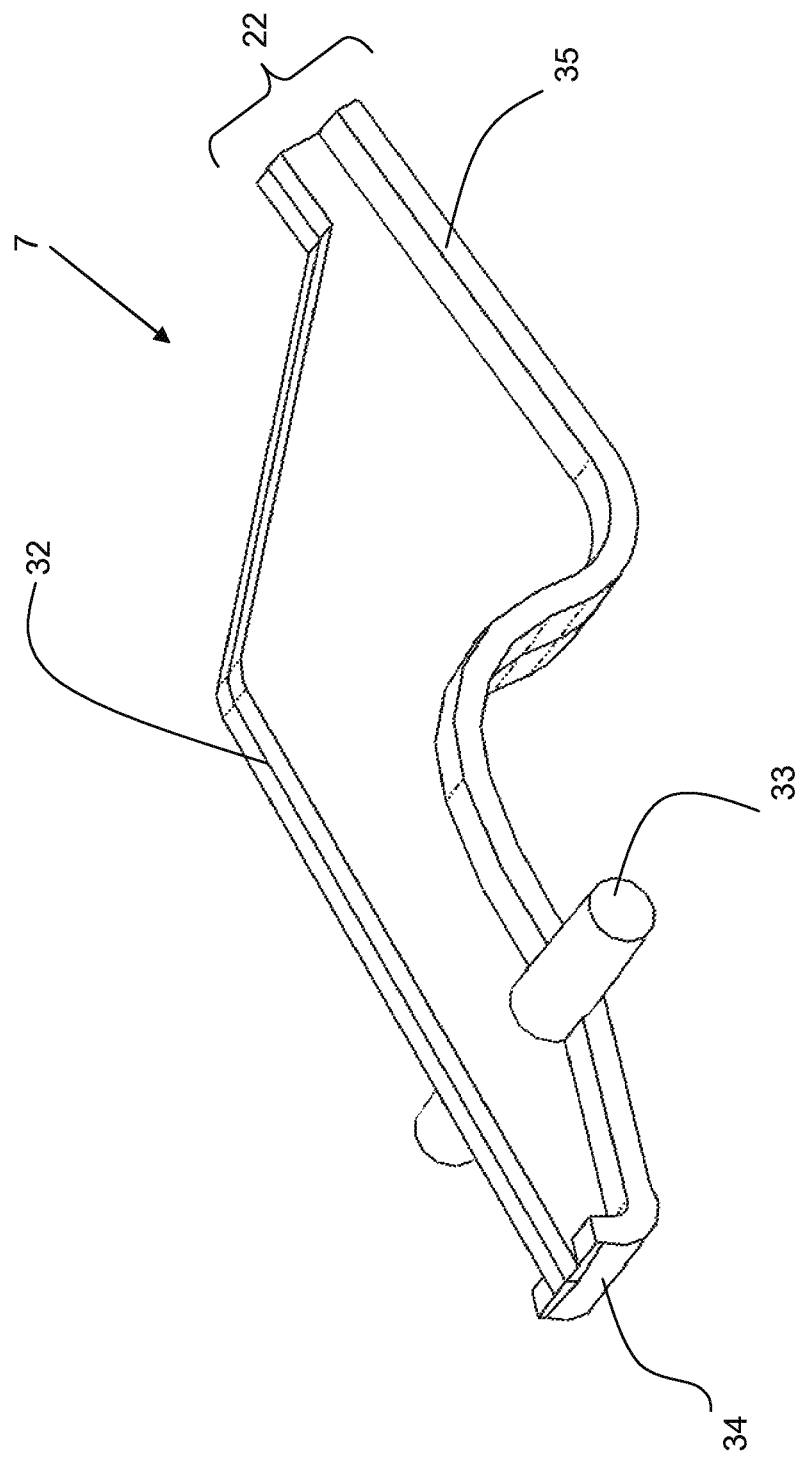
FIG. 16 depicts a perspective view of a actuator lever

FIG. 16 depicts an expanded view of an actuator lever 7 having one or more ribs 32, the ribs contoured to avoid contact with other components within a staple mechanism housing. An actuator lever 7 may have one or more pivot pins 33, sometimes used to rotate within a pivot void 31 of a staple housing mechanism. A block contact area 34 is sometimes used as a contact area or interface with staple folder block 10. The curved design of the block contact area provides a smooth interface and operation with a staple folder block. A wide rib 35 provides rigidity to the actuator lever and distributes actuating force from the actuator grip lever 5. A distal section 22 of the actuator lever may extend from staple mechanism housing and is rotated by a pivoting the actuator grip handle to fold staples.

Figure 17:
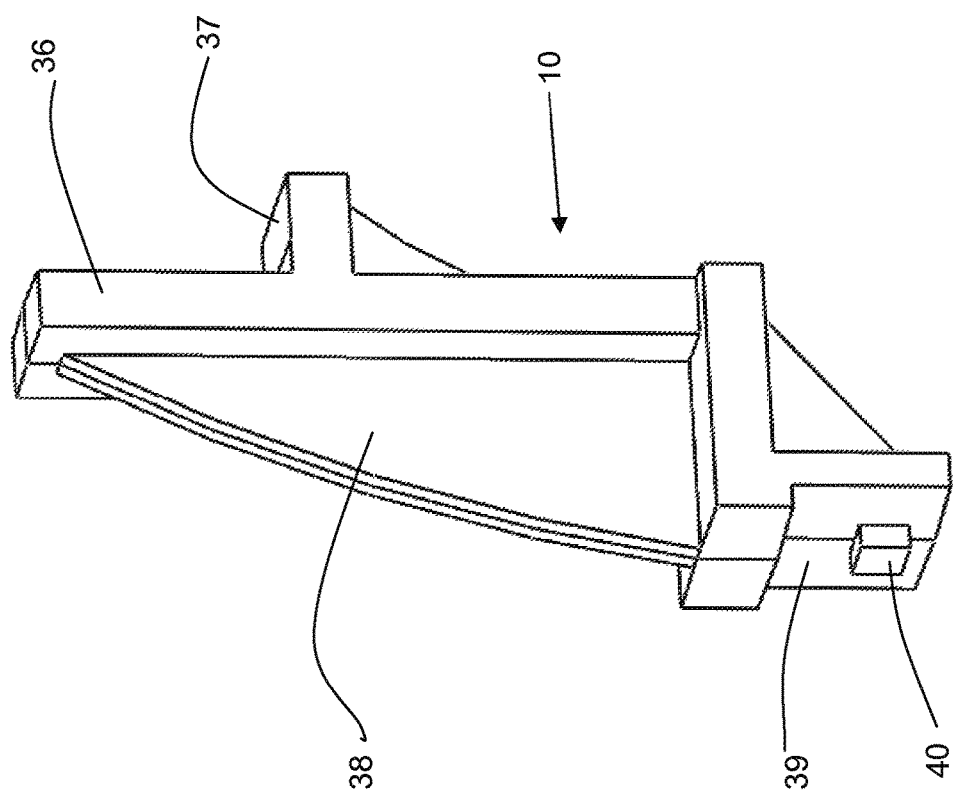
FIG. 17 depicts a perspective view of a staple folder block

FIG. 17 depicts an expanded view of a staple folder block 10 having a protruding surface 37 sometimes used to contact an actuator lever 7. A vertical rib 36 may be fitted or run in a vertical track 30 of the staple mechanism housing 15. A staple folder block may have one or more ribs 38, sometimes used to evenly distribute force to a staple folder plate 11. A recessed area 39 of the staple folder block 10 is sometimes used with a staple folder plate. The recessed area may have a raised block 40 sometimes used in connection with a void within a staple folder plate 11.

Figure 18:
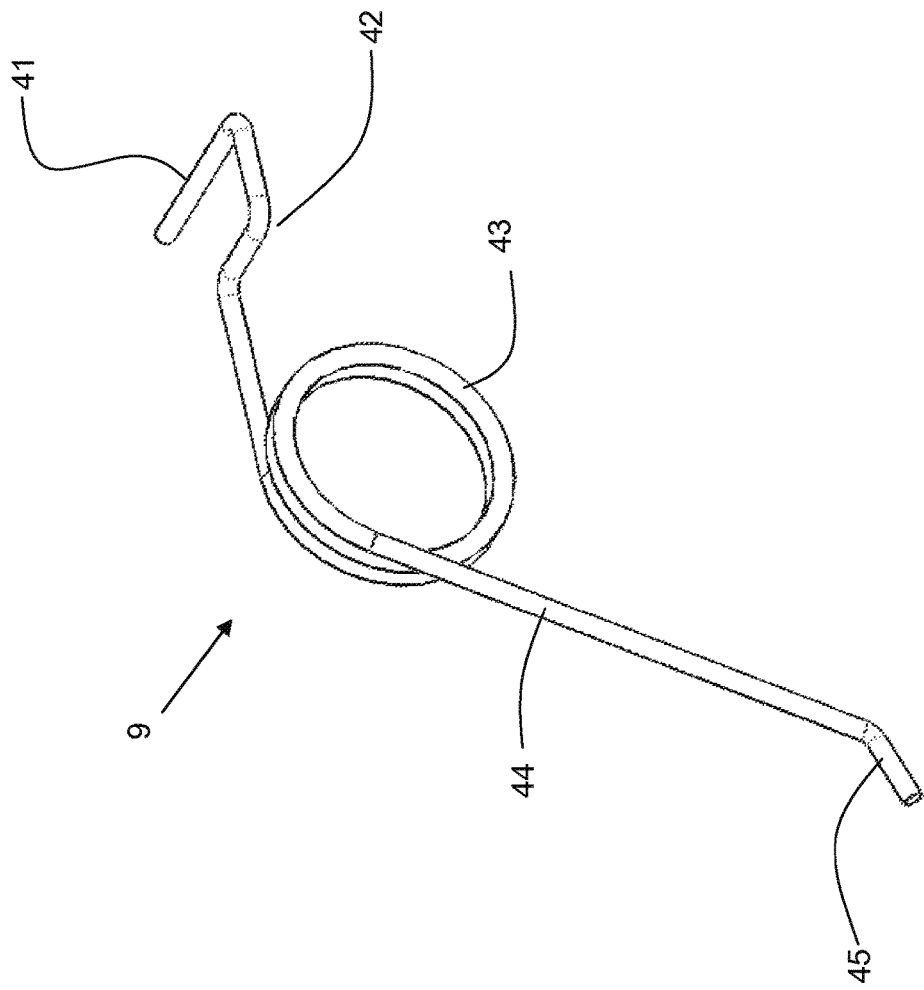
FIG. 18 depicts a perspective view of a staple advance spring

FIG. 18 depicts a staple advance spring 9 having a pivot leg 41 sometimes being inserted into a void within staple mechanism housing. An offset 42 centers the staple advance spring within the staple mechanism housing 15. The staple advance spring has a triple loop 43 which assists in keeping the spring within intended limits of elasticity. A pusher leg 44 flexes around the triple loop to advance staples. A leg 45 of the staple advance spring mates with a staple advance block 13.

Figure 19:
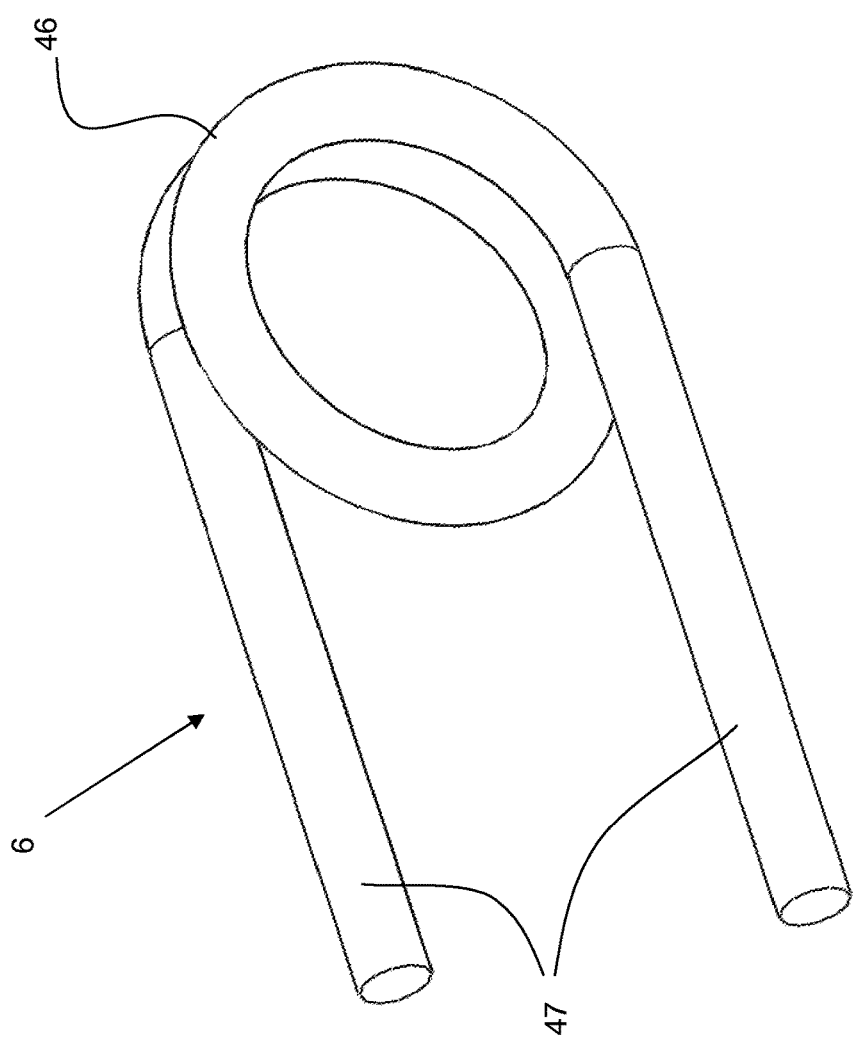
FIG. 19 depicts a perspective view of a return spring

FIG. 19 depicts a return spring 6 or staple folder having a double loop 46, keeping the spring within intended limits of elasticity. The legs 47 of the return spring 6 urge a staple folder block 10 back to a starting position.

Figure 20:
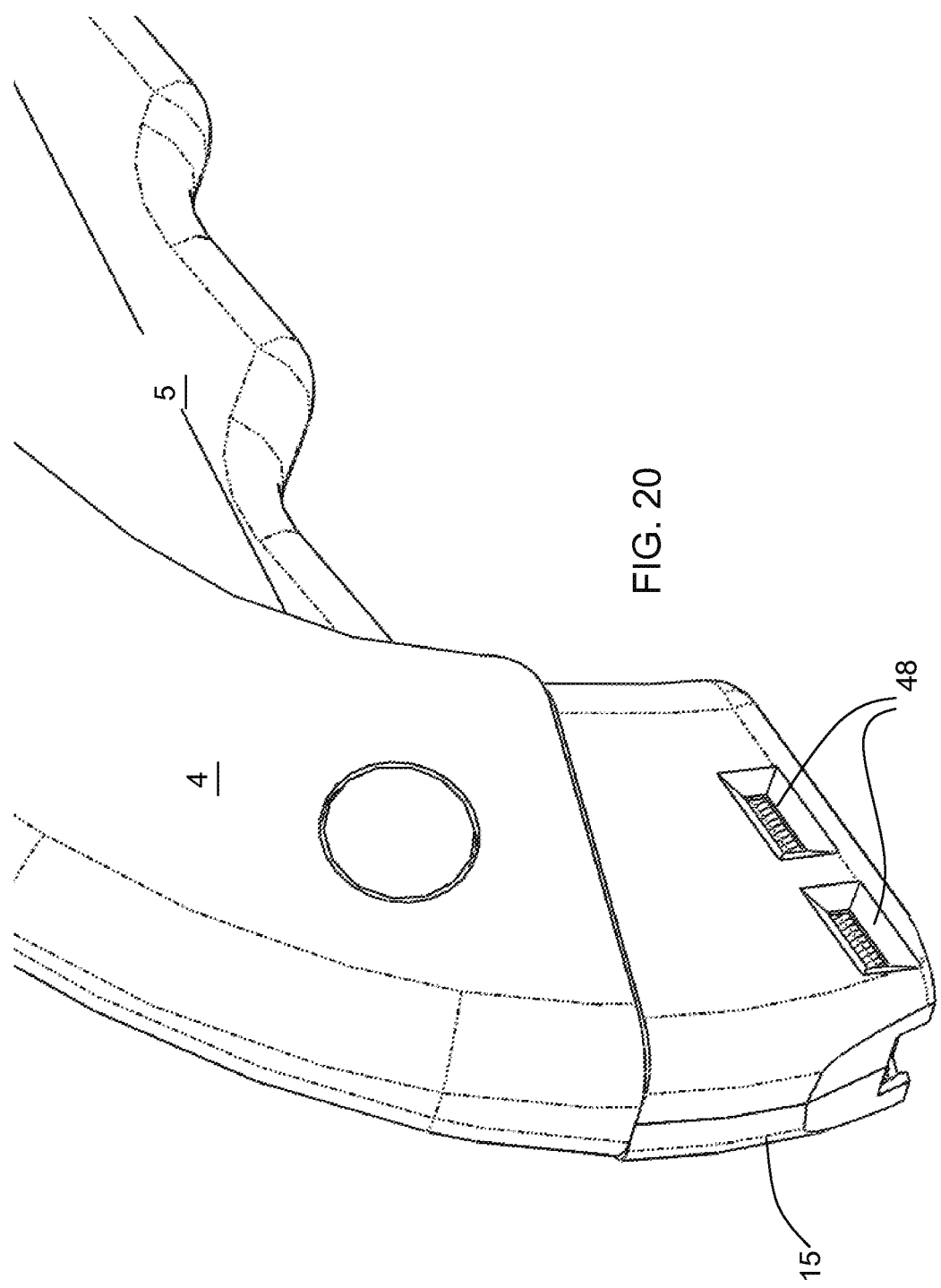
FIG. 20 depicts a perspective view an disclosed surgical stapler having a void area for viewing remaining staples

FIG. 20 depicts a perspective view of staple mechanism housing 15 inserted into a handle 4, with the staple mechanism housing having one or more voids 48 sometimes used to view the quantity of remaining staples.

Figure 21:
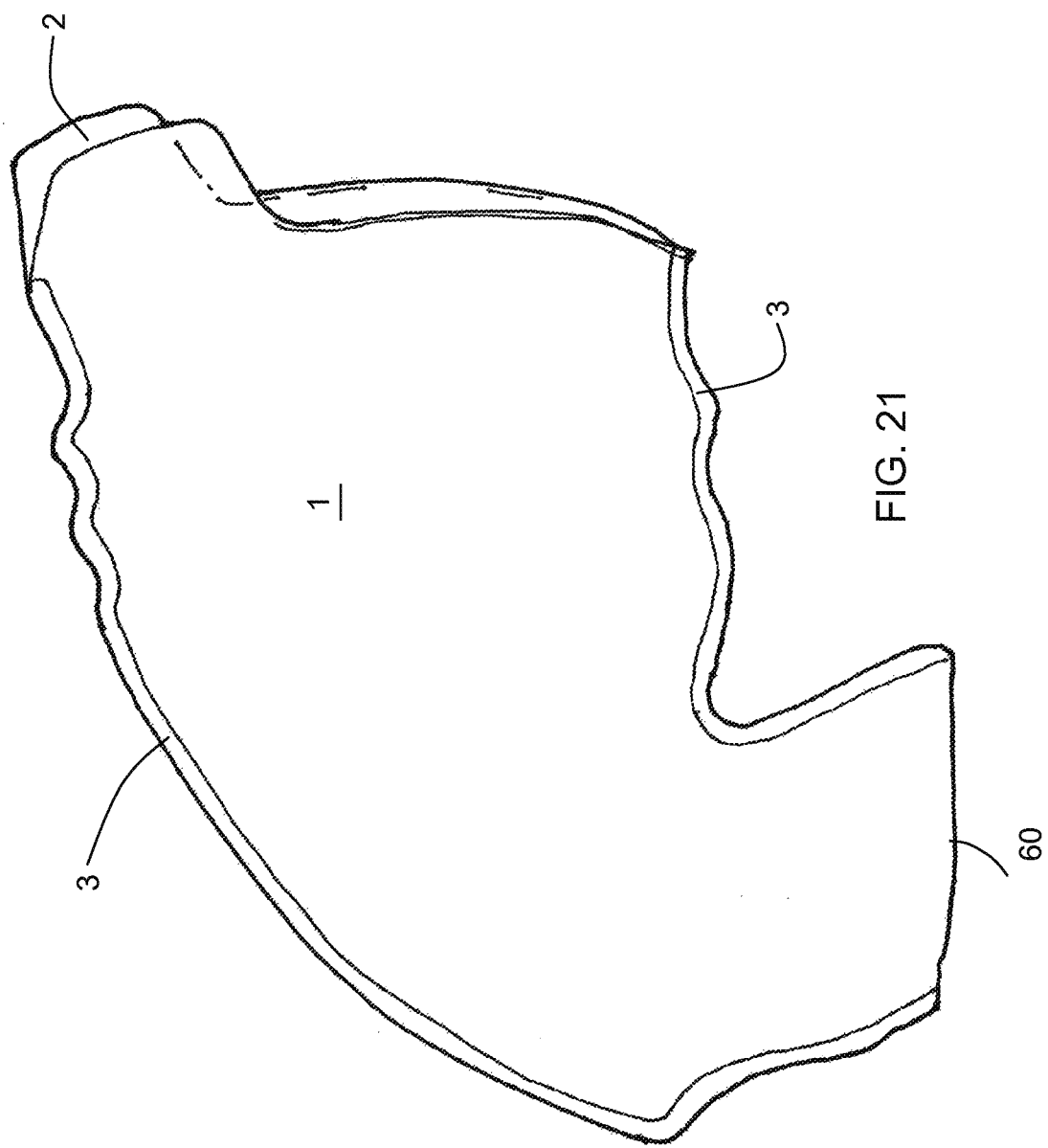
FIG. 21 depicts a disclosed sheath

FIG. 21 depicts a perspective view of a sheath having grip tabs 2 shown in an open position wherein back edges are unsealed to allow for insertion of a handle assembly. Along the sealed perimeter, seam sections 3 are shown. The seam sections may be sealed with adhesive to allow the seams to be torn open for clean waste disposal of a handle assembly. The sheath is shown with a folded edge 60 having no seam. This folded edge 60 section is sometimes adhesively attached to a point or line upon a superior side 65 of a staple housing mechanism. An attachment point 19, (shown on FIG. 7) secures the folded edge 60 of the sheath with a superior side of a staple housing.

FIG. 22 depicts a side view of a handle assembly inserted into a sheath with a section of loose sheath 70 having a folded edge attached to a stapler mechanism housing by use of adhesive, heat seal, mechanical clip or other fastening methods.

FIG. 23 depicts a final assembly of a skin stapler or surgical stapler having a fully sealed sheath and inserted staple mechanism housing.

FIG. 24 depicts grip tabs in a pulled apart position, exposing portions of a handle assembly. FIG. 25 depicts a fully exposed handle assembly with a sheath pulling staple mechanism housing out of a handle assembly. FIG. 26 depicts a housing assembly separated from a staple mechanism housing.

Figure 27:
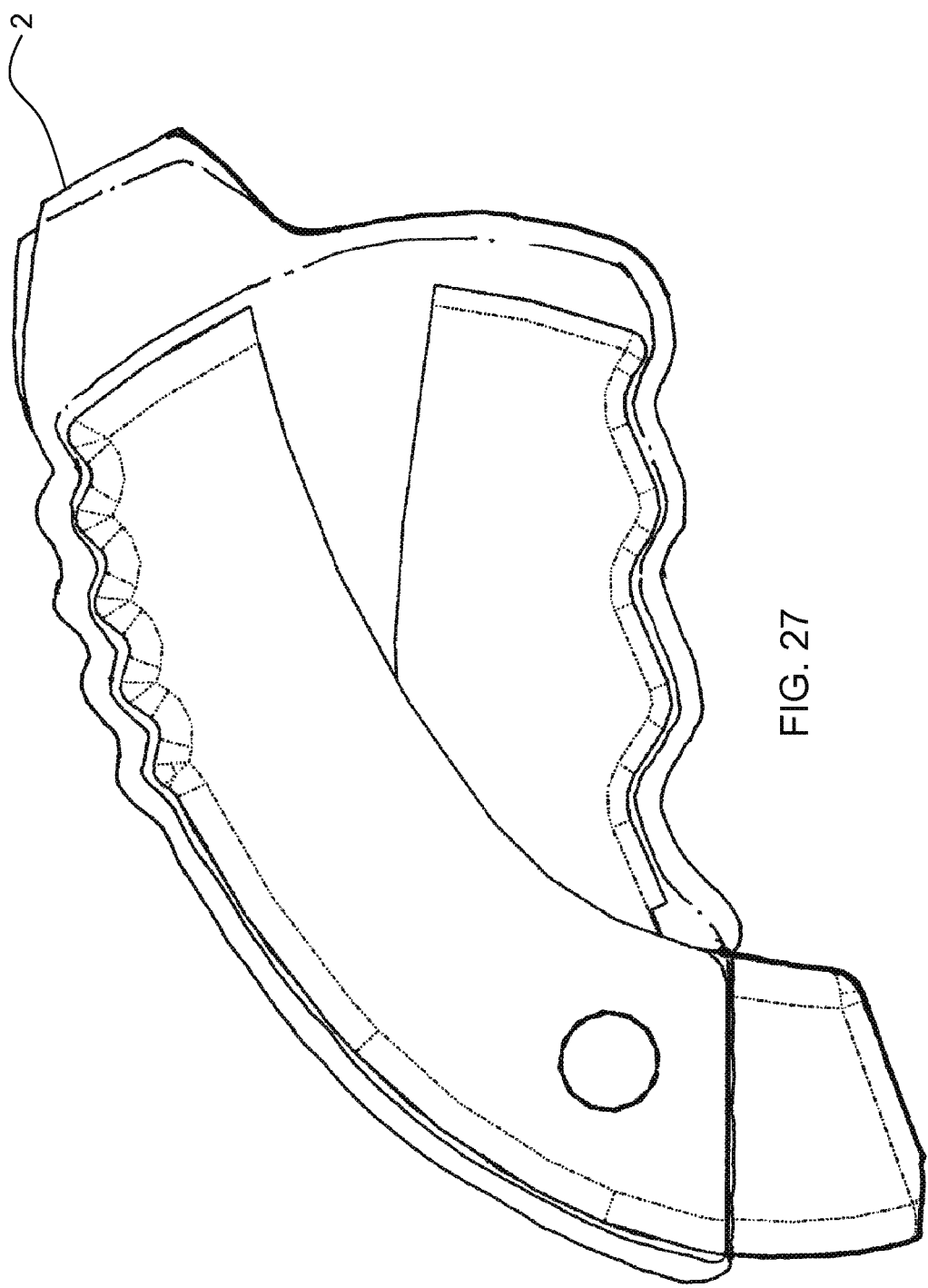
FIG. 27 depicts a surgical stapler with tabs for sheath removal

FIG. 27 depicts an assembled skin stapler or surgical stapler with a sealed sheath in place, the sheath having grip tabs.

Figure 28:
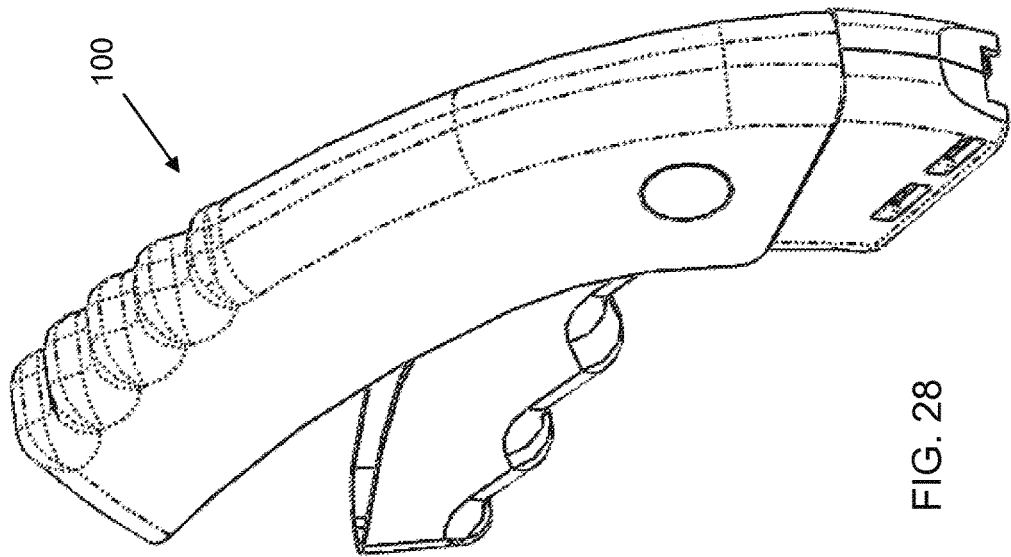
FIG. 28 depicts a surgical stapler in general

FIG. 28 depicts a skin stapler 100 in general, not having a sheath. The device is also sometimes referred to a surgical stapler.

Figure 29:
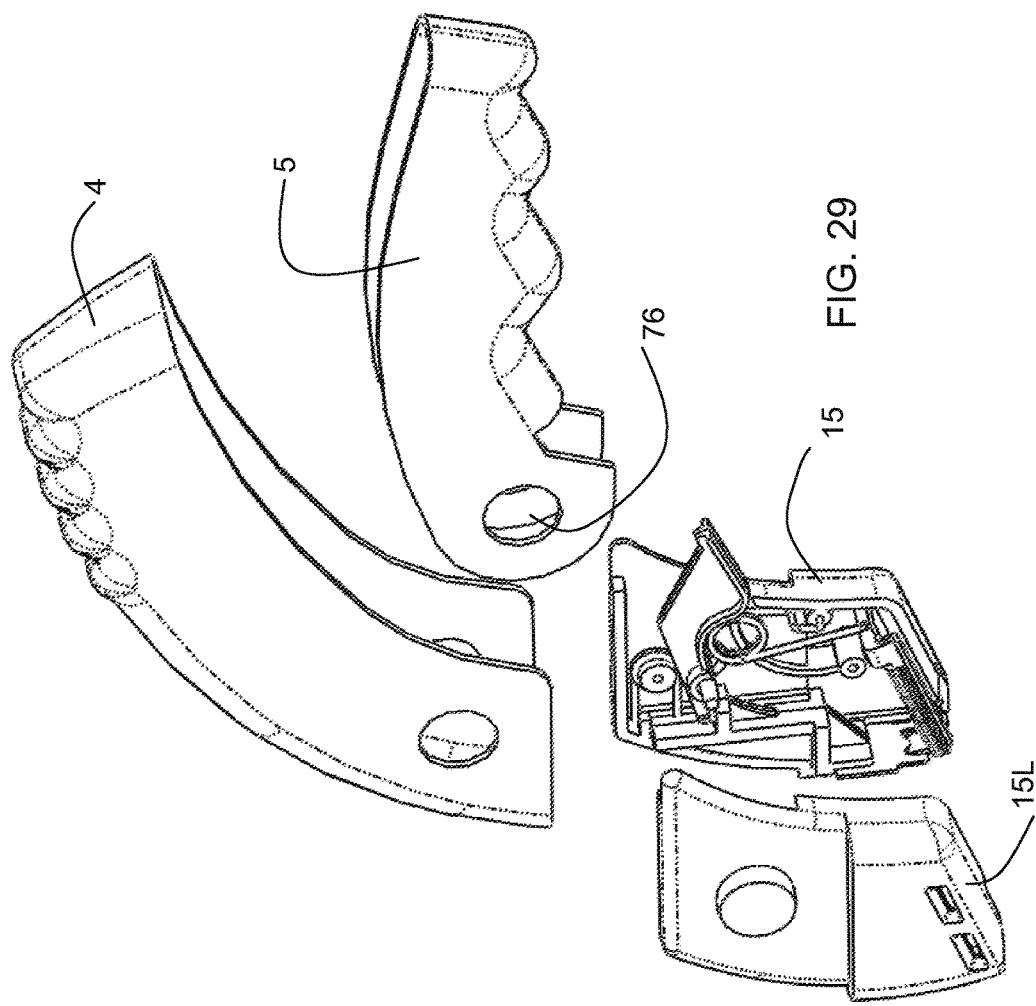
FIG. 29 depicts a surgical stapler components

FIG. 29 presents a handle 4, actuator grip lever 5 having a void 76 or center void sometimes used to mate with a boss 21. A left side 15L of staple mechanism housing is shown with a boss or actuator grip pivot. A right side 15R of staple mechanism housing is shown with a staple folder block, staple folder plate and metal staple carrier.

Figure 30:
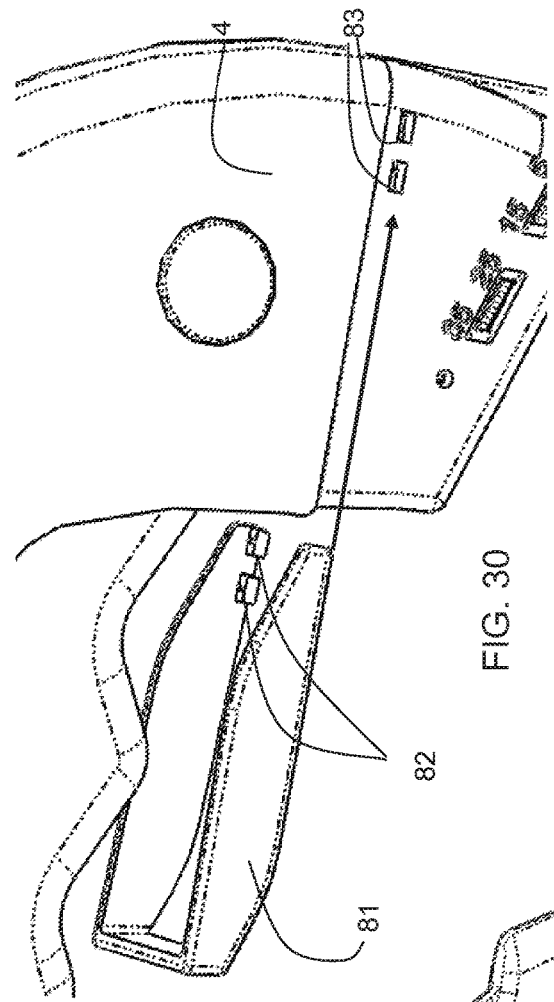
FIG. 30 depicts a handle retainer prior to assembly

FIG. 30 depicts a handle retainer prior to assembly and comprises an actuator grip lever, sometimes made of Molded Pulp Fiber or MPF, the handle retainer 4 comprising one or more assembly voids 83 for handle retainer bosses. A handle retainer 81 comprises one or more assembly bosses 82 with interference fit ribs.

Figure 31:
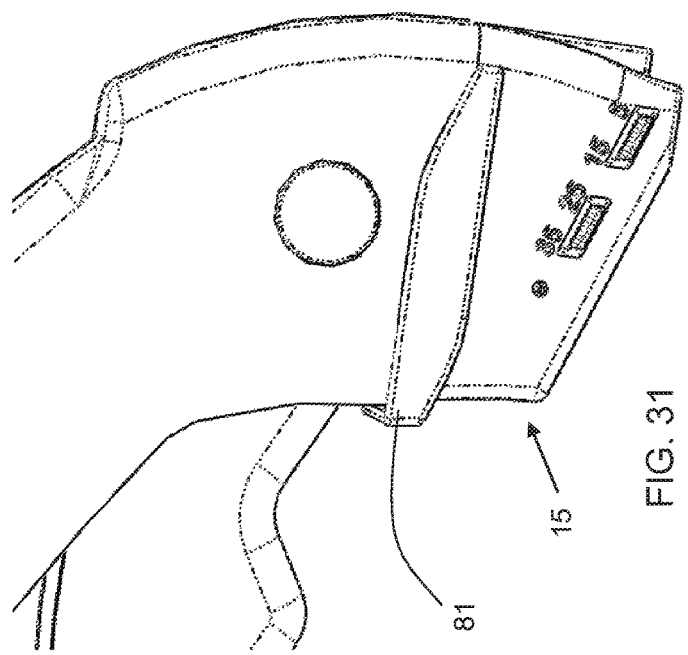
FIG. 31 depicts an assembled handle retainer

FIG. 31 depicts a handle retainer 81 attached to a handle. The attachment system may comprise the handle retainer mated to the handle by the insertion of assembly bosses with interference fit ribs 82 into assembly voids 83 for the handle retainer bosses.

Figure 32:
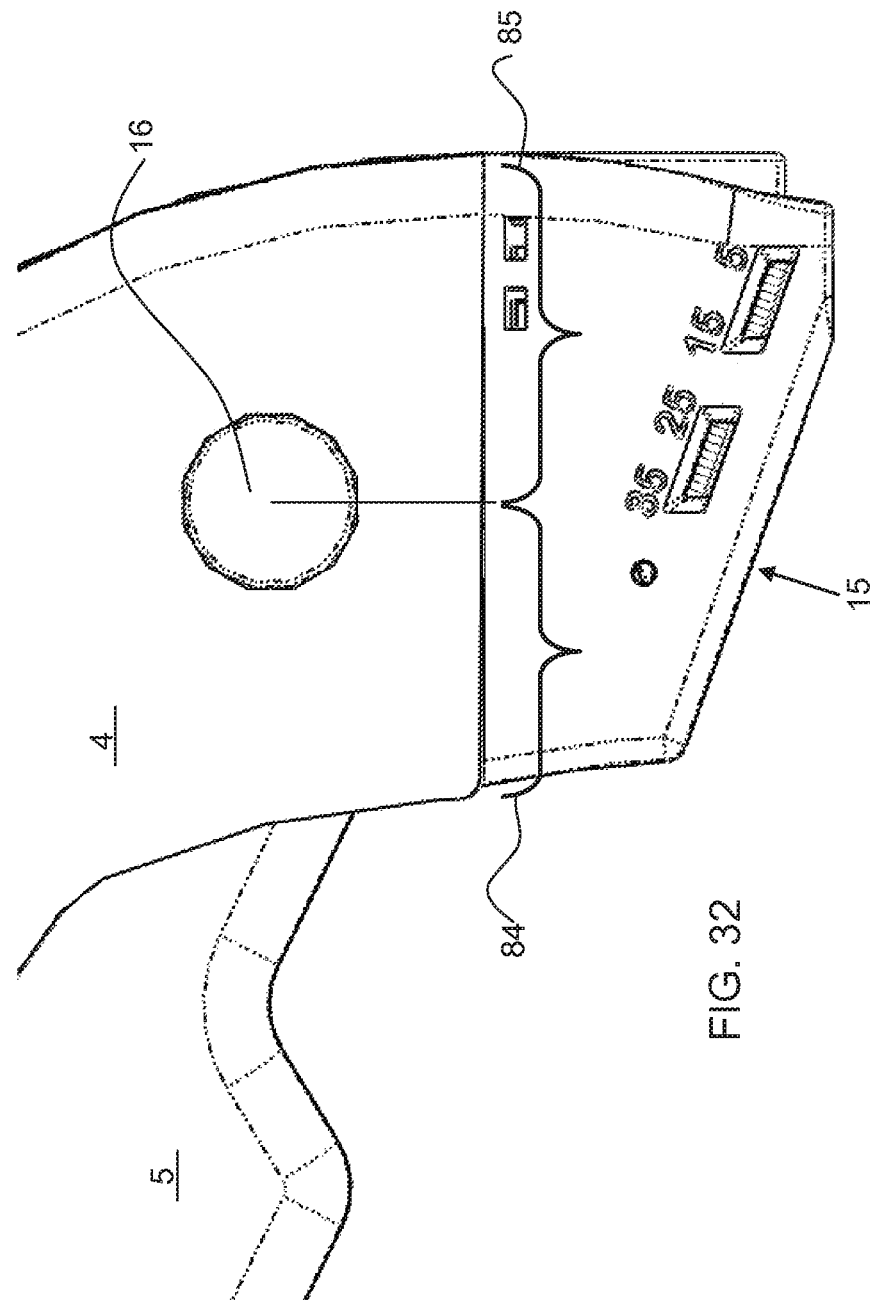
FIG. 32 depicts a proximal to distal configuration from a handle to the center of a raised circular boss

FIG. 32 depicts the relative positioning of a raised circular boss 16 as being centered along a lateral edge 67 of the handle 4. In one embodiment, the center point 89 of the raised circular boss 16 is centered along the lateral edge 67 of the staple housing mechanism. Section 84 depicts a proximal configuration or proportions of the handle with respect to the position of the raised circular boss 16. Section 85 depicts a distal configuration or proportions of the handle with respect to the position of the raised circular boss 16.

Figure 33:
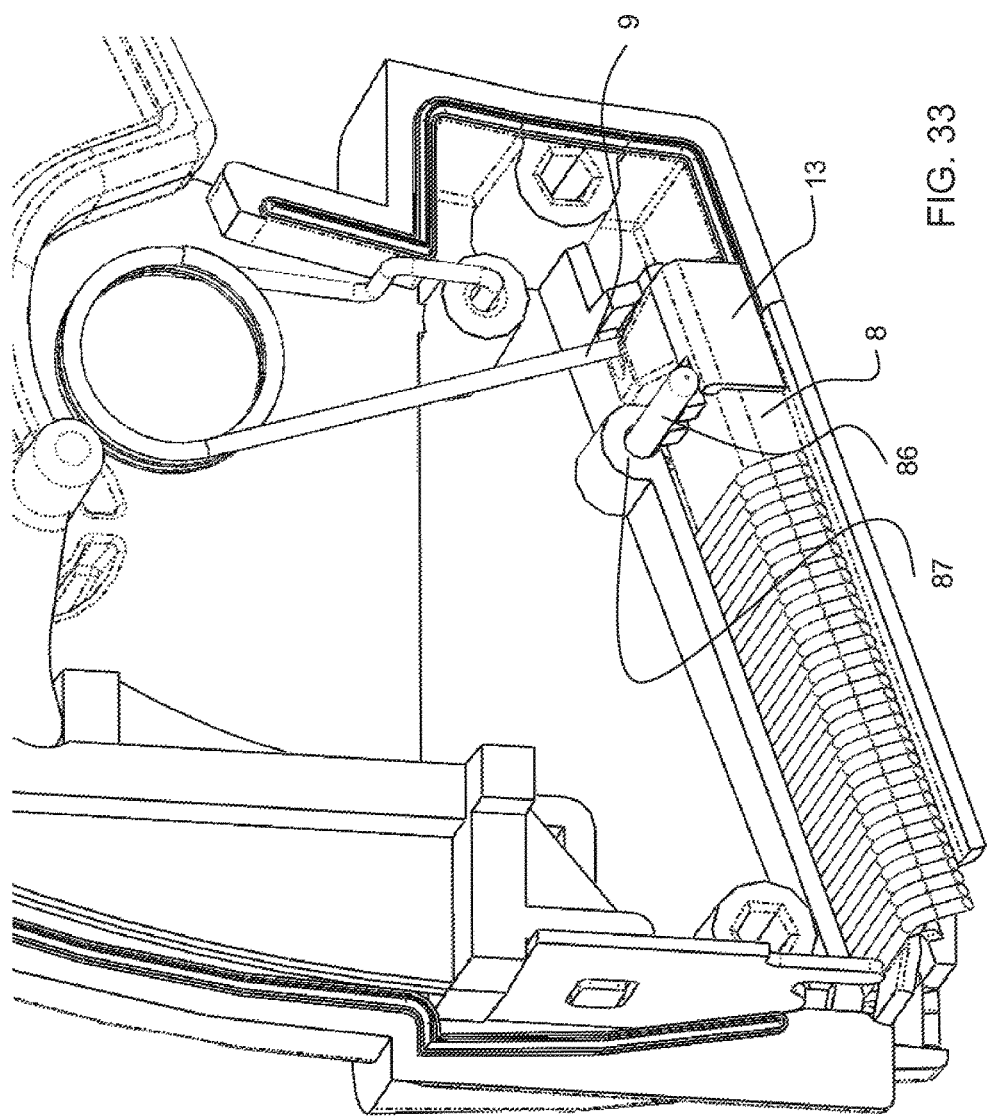
FIG. 33 depicts a staple carrier assembly fixture pin

FIG. 33 depicts a staple system comprising a staple advance spring 9 in tension with a staple advance block 13, the staple advance block sliding upon or otherwise connected to staple carrier tray 8. A staple carrier assembly fixture pin 86 is shown to mate or intersect with a locator void 87.

Figure 34:
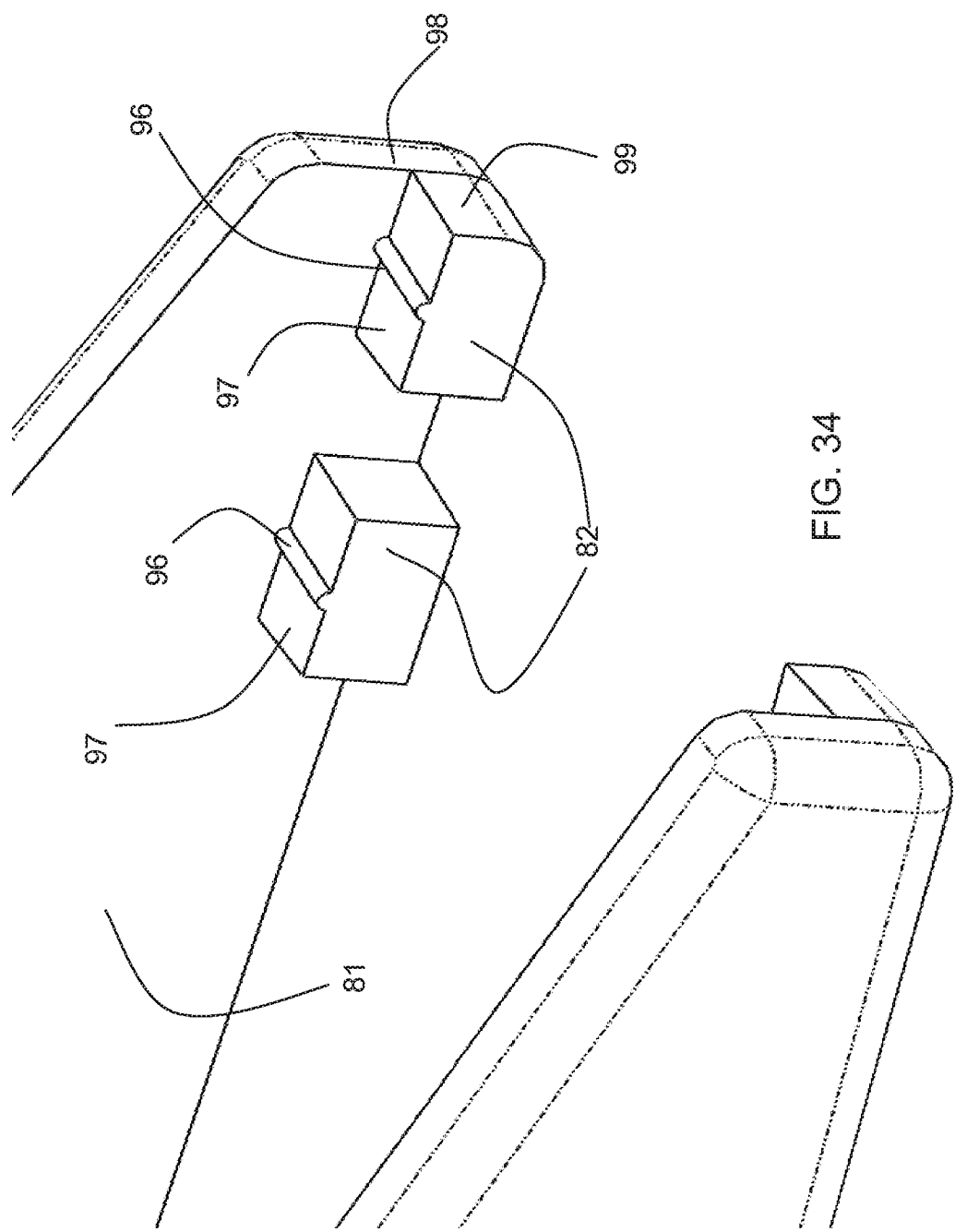
FIG. 34 depicts an expanded view of a handle retainer

FIG. 34 depicts an expanded view of the handle retainer 81 shown in FIG. 30. The handle retainer 81 may comprise one or more assembly ribs 82. Each assembly rib may comprise an upper shelf 97 that supports an interference fit rib 96. A distal assembly rib may comprise a distal surface 99 conforming to the distal surface 98 of a handle retainer. The configuration of the interference fit ribs 96 and adjoining shelf 97 facilitate the efficient mating of the assembly ribs 82 into the assembly voids 83.

Figure 35:
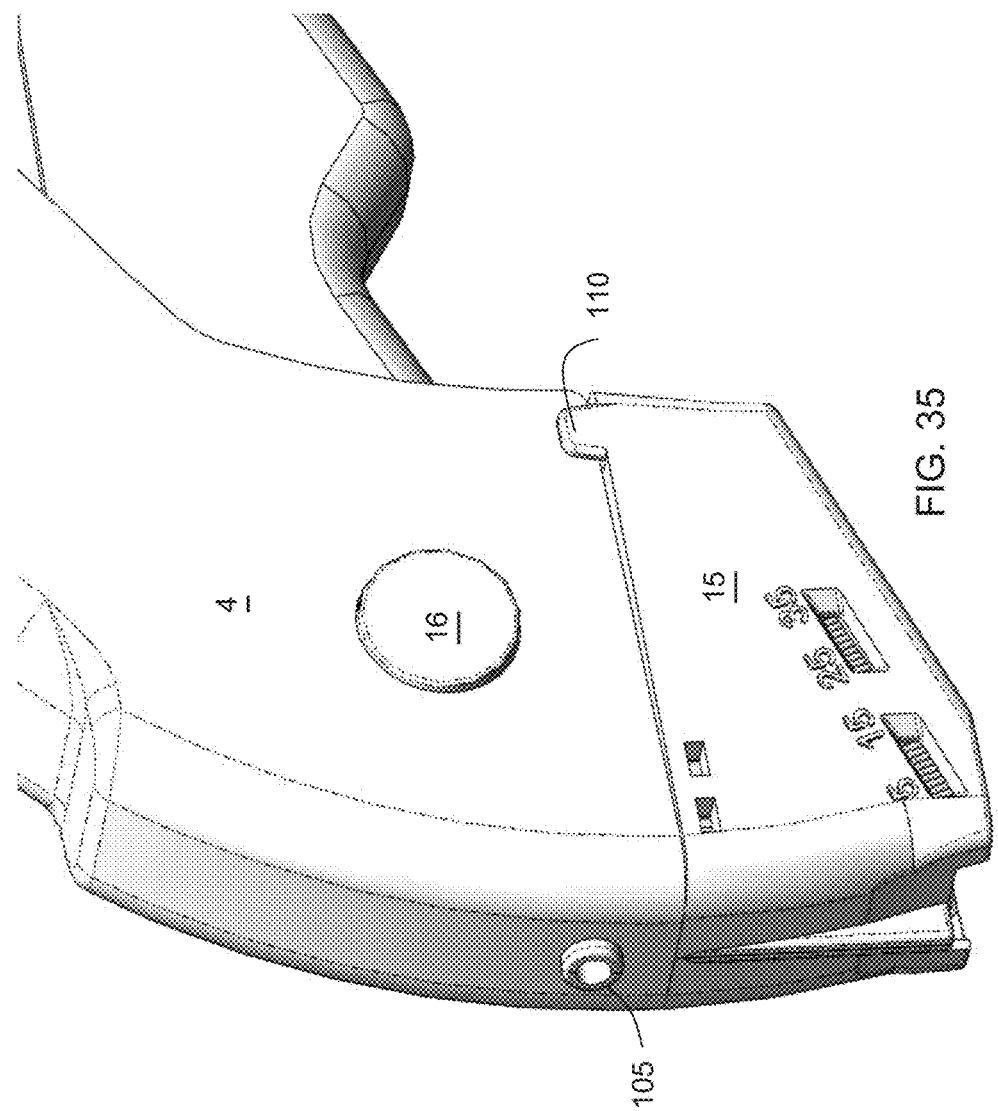
FIG. 35 depicts a perspective view of an embodiment featuring handle retainer ears and a handle alignment pin

FIG. 35 depicts a handle 4 having a handle alignment pin 105. The handle alignment pin resists rotation around the handle pivot boss 16. The handle alignment pin may be fixed to the interior portions of the stapler mechanism and protrude through a void of the handle.

FIG. 35 depicts handle retainer ear 110 which is attached to or part of the staple mechanism housing 15. The staple mechanism housing may comprise two retainer ears. Each retainer ear 110 has an inside surface that prevents outward flexing of the adjacent handle 4. The new handle retainer ear system replaces the retainer clip. Each handle retainer ear 110 prevents flexing or distortion of the lower sections of the MPF handle 4. Each handle retainer ear 110 may be positioned toward the rear or posterior section of the handle to achieve maximum mechanical advantage in preventing flex in the handle.

Figure 36:
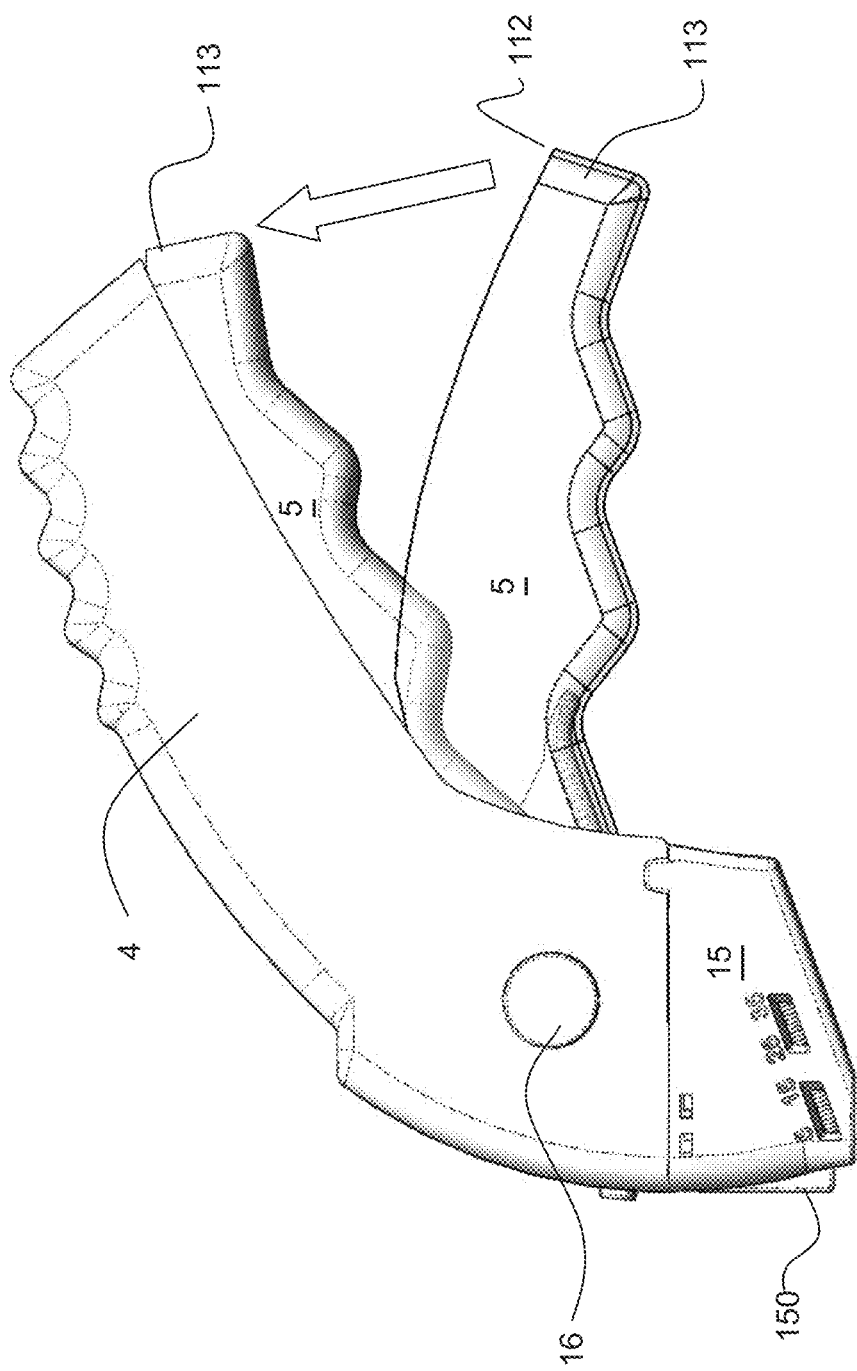
FIG. 36 depicts a plan view of a lever grip being stopped by the back end of a handle

FIG. 36 depicts a lever grip 5 in two positions relative to the handle 4. The improved lever grip 5 comprises a rear or posterior arched rear section 113 that protrudes past the rear section of the handle 4. The arched rear section 113 of the lever grip provides a positive and nondestructive stop against the handle. The positive stop system significantly reduces the stresses or forces placed upon the MPF parts, such as the handle. In general the lever grip 5 rotates around the pivot boss 16 and the lever grip 5 reaches a positive stop against the handle 4. FIG. 36 also depicts a new alignment indicator 150 that is attached to or part of the staple mechanism housing 15.

Figure 37:
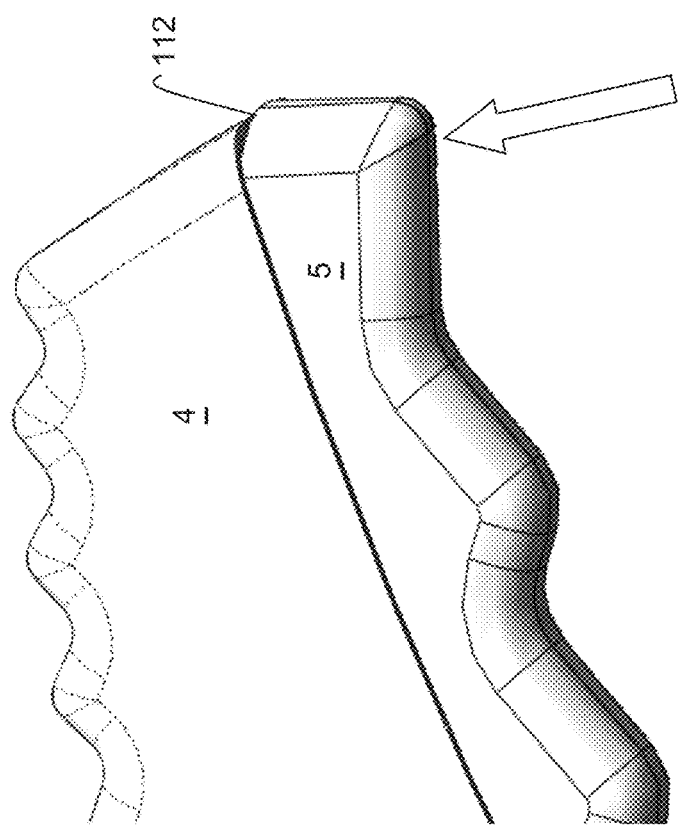
FIG. 37 depicts a perspective view of a lever grip being stopped by the back end of a handle

FIG. 37 depicts a lever grip 5 stopped upon a handle 4.

Figure 38:
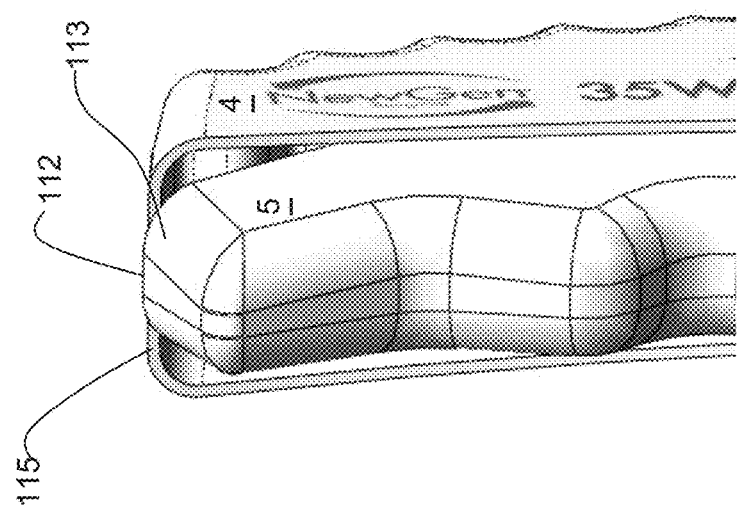
FIG. 38 depicts a perspective view of a lever grip being stopped by the back end of a handle

FIG. 38 depicts a positive mating area 112 of the rear section of the lever 5 stopped upon or at the positive mating area 115 of the rear section of the handle 4. The positive matting area 112 of the rear section of the lever grip may be part of the arched rear section 113 of the lever grip.

Figure 39:
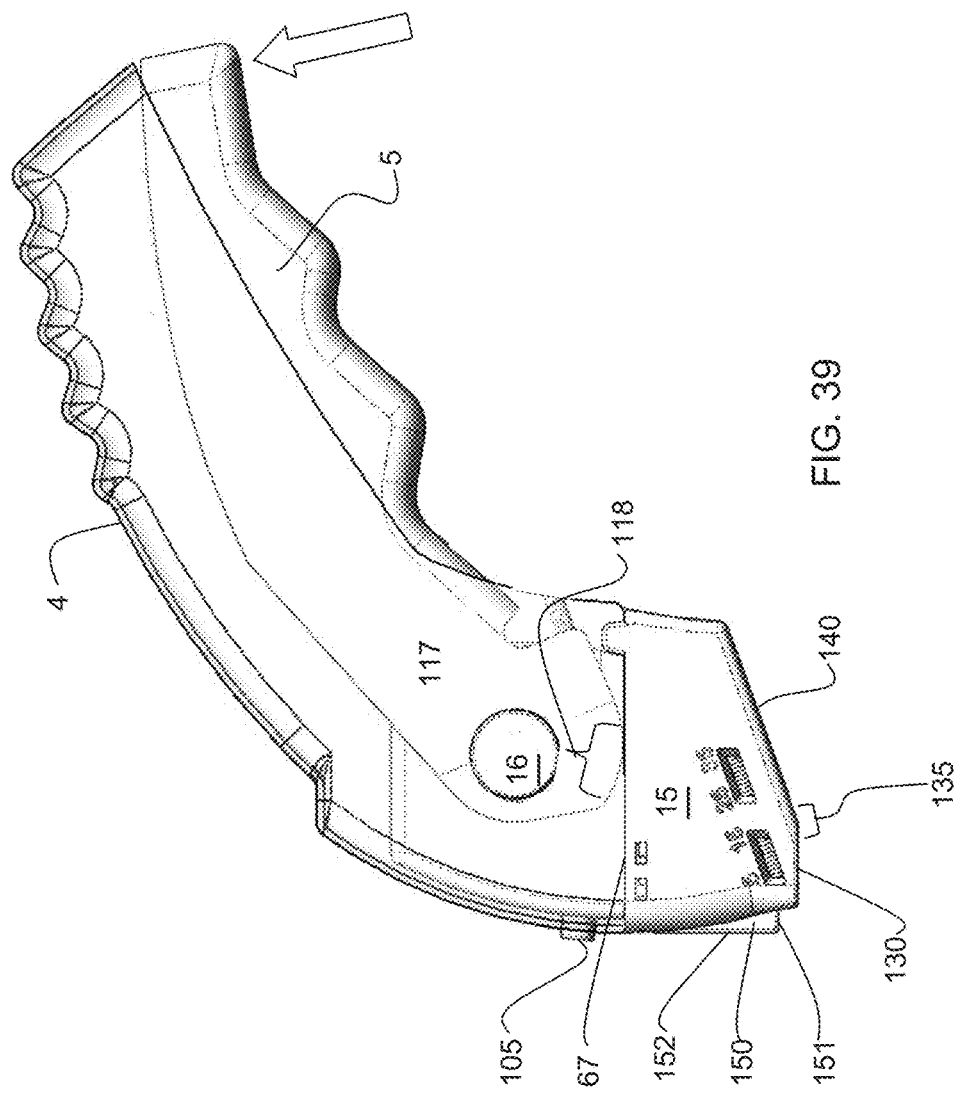
FIG. 39 depicts a plan view of a lever grip stopped at the end of a handle

FIG. 39 depicts various features of the staple mechanism housing 15, handle 4 and lever grip 5. In general the lever grip 5 may rotate around the handle pivot boss 16 to trigger or facilitate the expulsion of staples. In order to make a lever grip 5 out of MPF many engineering challenges were overcome. To wit, the rotational forces exerted at the front section of the lever 5 are artfully dissipated over a wide area by the use of a concentrically trimmed arc 118 of the lever grip sidewalls 117. The concentrically trimmed arcs of the lever grip sidewalls may be concentric to the pivot boss 16. The arcs 118 may travel upon the lateral edge 67 of the staple housing mechanism.

FIG. 39 further depicts a new alignment indicator 150 attached to the staple mechanism housing 15. In general, the disclosed stapler may be viewed by a surgeon in the same perspective shown in FIG. 39. Thus, the alignment indicator 150 is highly visible and acts as a plumb line reference point to keep the stapler in a proper angle. In particular the front vertical section 152 is to be kept in a vertical angle and the lower horizontal section 151 is to be kept horizontal. Moreover, as a further visual guide quality, the lower horizontal section 151 of the guide rod is on the same plane or is parallel to the stapler guide 130 of the staple mechanism housing 15.

The flattened stapler guide 130 of the staple mechanism housing is intended to be positioned flat upon the patient. A rear lower section 140 of the staple mechanism sweeps upwardly to minimize patient contact. The transition point or transition angle 135 between the flattened stapler guide 130 and the lower edge section 140 may be between 10 to 35 degrees.

FIG. 40 depicts a new return spring 120 comprising an upper leg 121, a lower leg 122 and an arch section 123. The arched section 123 may define a void used to accept a spring locating boss 125. The upper leg 121 may be fitted or retained into an upper section of the staple mechanism housing 15. The lower leg 122 may fit into or press upon the staple folder block 10. The unique contour of the return spring facilitates full travel of the folder block without the return spring fouling or being impeded by adjacent components.

Items

Disclosed embodiments include the following items or descriptions.

Item 1. A surgical stapler system comprising:

a) a handle 4 having two center voids 75, an interior void 77 defined by exterior walls of the handle;

b) an actuator grip lever 5 having two center voids 76;

c) a staple mechanism housing 15 having one or more handle pivot bosses 16 fitted to fill the two center voids of 75 of the handle 4 and fitted to fill the two center voids 76 of the actuator grip lever 5, the staple mechanism housing 15 having a narrow section 66 attached to the bosses 16 and the narrow section fitted for insertion into the handle and actuator grip lever, the narrow section attached to a plurality of lateral ridges 67 and the plurality of lateral ridges attached to a base section 68, the base section fitted to not insert into either the handle 4 or actuator grip lever 5.

d) the staple mechanism housing further comprising two retainer ears 110 with each retainer ear located at a rear section of the staple mechanism housing.

e) the actuator grip lever comprising two lever grip sidewalls 117 with each sidewall comprising a concentrically trimmed arc.

f) the staple mechanism housing further comprising a alignment indicator 150, the alignment indicator comprising a lower horizontal section 151 and a front vertical section.

g) the staple mechanism housing further comprising a flattened stapler guide 130 and a rear lower edge section 140.

Item 2. The system of item 1 wherein the narrow section 66 of the staple mechanism housing 15 is further defined by a superior side 65.

Item 3. The system of item 2 wherein the actuator grip lever 5 is in connection with a distal section 22 of an actuator lever 7, the actuator lever connected to the staple mechanism housing.

Item 4. The system of item 3 wherein the staple mechanism housing further comprises a right side component 15r and a left side component 15l, and the actuator lever 7 comprises one or more curved ribs 32, connected to a block area 34, wide rib 35 and one or more pivot pins 33, with a pivot pin 33 connected to a pivot void 31 defined by a side component 15r or 15l of the staple mechanism housing, the side component comprising a boss 24, a curved rib 25 a pivot void 26 a recess 27, a track 28, a front inside wall 29, and a vertical track 30.

Item 5. The system of item 4 wherein a return spring 120 comprises an upper leg 121 retained within an upper portion of the staple mechanism housing, a lower leg 122 retained within a staple folder block 10, the return spring attached to the staple mechanism housing with a spring locating boss the staple mechanism further comprising a staple advance spring 9, the pivot void is attached to the staple advance spring 9, the recess 27 holds a staple carrier tray 8, the track 28 holds a staple folder plate 11, the front inside wall 29 retains a staple, and the vertical track 30 retains the staple folder block.

Item 6. The system of item 5 wherein the staple mechanism housing further comprises a staple carrier assembly fixture pin 86 attached within a staple carrier assembly fixture pin locator void 87.

Item 7. The system of item 6 wherein the stable advance block is held in tension against the assembly fixture pin.

Item 7.7 the system above wherein the lever comprises a positive mating area 112 comprising a arched rear section 113.

Item 8. A method of protecting stapler components for clean bin recycling, the method comprising the steps of:

a) using a sheath 1 to cover a handle assembly 80, the handle assembly comprising a handle 4 and a actuator grip lever 5;

b) using a loose section 70 of the sheath to cover a narrow section 66 of a staple mechanism housing 15 and to cover one or more handle pivot bosses 16;

c) using a folded edge 60 of the sheath to attach to a superior side 65 of the staple mechanism housing;

d) sealing the sheath 1 along seams 3 and encasing the handle assembly 80;

d) using grip tabs 2 upon the sheath to pull the sheath from the handle assembly and releasing the handle assembly.

Item 9. The method of Item 8 including the step of using paper pulp material in the construction of the handle assembly.

Item 10. The method of item 9 including the step of dropping the handle assembly into a container, the container used for holding recyclable material.

Item 11. The method of claim 1 using lateral ledges 67 upon the staple housing mechanism 15 as stopping block to stop the further insertion of the staple housing mechanism into the handle assembly.

Item 12. A surgical stapler kit comprising:

a) a handle assembly 80 comprising a handle 4 and a actuator grip lever 5; and b) a staple mechanism housing 15 comprising a narrow section 66, a superior side 65, lateral ledges 67 and a base section 68.

Item 13. The kit of item 12 wherein the staple mechanism housing further comprises a right side 15R component and a left side 15L component, with each side component comprising a boss 24, a curved rib 25, a pivot void 26, a recess 27, a track 28, a front inside wall 29 and a vertical track 30.

Item 14. The kit of item 13 further comprising a return spring 120, an actuator lever 7, a staple carrier tray 8, a staple advance spring 9, a staple folder block 10, a staple folder plate 11, a staple stack 12, and a staple advance block 13.

Item 15. The kit of item 14 wherein the actuator lever 7 is comprised of a distal section 22, on or more curved ribs 32, a block contact area 34, a wide rib 35 and one or more pivot pins 33.

Item 16. The kit of item 14 wherein the staple folder block comprises one or more vertical ribs 38, one or more curved ribs 38, a protruding surface 37, a recessed area 39 with the recessed area including a raised block 40.

Item 17. The kit of item 14 wherein the staple advance spring 9 is comprised of a pivot leg 41, an offset 42, a plurality of loops 43, a pusher leg 44 and a leg 45.

Item 18. The kit of item 14 wherein the return spring 6 comprises a plurality of loops 46 and two legs 47.

Item 19. The kit of item 14 wherein the base section 68 of the staple mechanism housing 15 includes a viewing void 48, FIG. 20.

Item 20. The kit of item 14 wherein the staple mechanism housing further includes a staple carrier assembly fixture pin attached within a locator void 87, the locator void defined within the staple carrier assembly.

What is claimed is:

1. A surgical stapler system comprising:
a) a handle having two center voids, an interior void defined by exterior walls of the handle;
b) an actuator grip lever having two center voids;
c) a staple mechanism housing having one or more handle pivot bosses fitted to fill the two center voids of the handle and fitted to fill the two center voids of the actuator grip lever, the staple mechanism housing having a narrow section attached to the bosses and the narrow section fitted for insertion into the handle and actuator grip lever, the narrow section attached to a plurality of lateral ridges and the plurality of lateral ridges attached to a base section;
d) the staple mechanism housing further comprising two retainer ears, with each retainer ear attached at a rear section of the staple mechanism housing;
e) the actuator grip lever further comprising two lever grip sidewalls with each lever grip sidewall comprising a concentrically trimmed arc;

f) the actuator grip lever further comprising an arched rear section; and g) staple mechanism housing further comprising a flattened stapler guide.

2. The system of claim 1 wherein the staple mechanism housing comprises an alignment indicator.

3. The system of claim 2 wherein the actuator grip lever is connected to a distal section of an actuator lever, the actuator lever connected to the staple mechanism housing.

4. The system of claim 3 wherein the staple mechanism housing further comprises a right side component and a left side component, and the actuator lever comprises one or more curved ribs, connected to a block area, wide rib and one or more pivot pins, with a pivot pin connected to a pivot void defined by a side component of the staple mechanism housing, the side component comprising a boss, a curved rib, a pivot void, a recess, a track, a front inside wall and a vertical track.

5. The system of claim 4 wherein a return spring comprises an upper leg retained within an upper portion of the staple mechanism housing, a lower leg retained within a staple folder block, the return spring attached to the staple mechanism housing with a spring locating boss, the staple mechanism further comprising the curved rib connected to a staple advance spring, the pivot void is attached to the staple advance spring, the recess holds a staple carrier tray, the track holds a staple folder plate, the front inside wall retains a staple, and the vertical track retains a staple folder block.

6. The system of claim 5 wherein the staple mechanism housing further comprises a staple carrier assembly fixture pin, the staple carrier assembly fixture pin attached within a staple carrier assembly fixture pin locator void, the locator void defined within the handle.

7. The system of claim 6 wherein the staple advance block is held in tension against the assembly fixture pin.

8. A method of protecting stapler components for clean bin recycling, the method comprising the steps of:

a) using a sheath to cover a handle assembly, the handle assembly comprising a handle and a actuator grip lever;

b) using a loose section of the sheath to cover a narrow section of a staple mechanism housing and to cover one or more handle pivot bosses;

c) using a folded edge of the sheath to attach to a superior side of the staple mechanism housing;

d) sealing the sheath along seams and encasing the handle assembly; and d) using grip tabs upon the sheath to pull the sheath from the handle assembly and releasing the handle assembly.

9. The method of claim 8 including the step of using paper pulp material in the construction of the handle assembly.

10. The method of claim 9 including the step of dropping the handle assembly into a container, the container used for holding recyclable material.

11. The method of claim 8 using lateral ledges upon the staple housing mechanism as a stopping block to stop the further insertion of the staple housing mechanism into the handle assembly.

12. A surgical stapler kit comprising:

a) a handle assembly comprising a handle and an actuator grip lever;

b) a staple mechanism housing comprising a narrow section, a superior side, lateral ledges and a base section;

c) the staple mechanism housing further comprises a right side component and a left side component, with each side component comprising a boss, a curved rib, a pivot void, a recess, a track, a front inside wall and a vertical track; and d) a return spring, an actuator lever, a staple carrier tray, a staple advance spring, a staple folder block, a staple folder plate, a staple stack and a staple advance block.

13. The kit of claim 12 wherein the actuator lever is comprised of a distal section, one or more curved ribs, a block contact area, a wide rib and one or more pivot pins.

14. The kit of claim 12 wherein the staple folder block comprises one or more vertical ribs, one or more curved ribs, a protruding surface, a recessed area with the recessed area including a raised block.

15. The kit of claim 12 wherein the staple advance spring is comprised of a pivot leg, an offset, a plurality of loops, a pusher leg and a leg.

16. The kit of claim 12 wherein the return spring comprises a plurality of loops and two legs.

17. The kit of claim 12 wherein the base section of the staple mechanism housing includes a viewing void.

18. The kit of claim 12 wherein the staple mechanism housing further includes a staple carrier assembly fixture pin and the handle defines a locator void.

\* \* \* \* \*